(12) United States Patent
Alajoki et al.

(10) Patent No.: US 6,989,128 B2
(45) Date of Patent: *Jan. 24, 2006

(54) APPARATUS FOR CONTINUOUS LIQUID FLOW IN MICROSCALE CHANNELS USING WICKING

(75) Inventors: Marja Liisa Alajoki, Palo Alto, CA (US); H. Garrett Wada, Atherton, CA (US); Robert S. Dubrow, San Carlos, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 10/142,263

(22) Filed: May 8, 2002

(65) Prior Publication Data

US 2002/0179445 A1   Dec. 5, 2002

Related U.S. Application Data

(63) Continuation of application No. 09/245,627, filed on Feb. 5, 1999, now Pat. No. 6,416,642.

(60) Provisional application No. 60/116,602, filed on Jan. 21, 1999.

(51) Int. Cl.
*B01L 3/02* (2006.01)
*G01N 27/453* (2006.01)

(52) U.S. Cl. .................. 422/50; 422/100; 204/601

(58) Field of Classification Search .............. 422/100, 422/50; 204/600, 601

See application file for complete search history.

(56) References Cited

U.S. PATENT DOCUMENTS

| | | |
|---|---|---|
| 4,731,335 A | 3/1988 | Brigati |
| 4,946,795 A | 8/1990 | Gibbons et al. |
| 5,009,760 A | 4/1991 | Zare et al. |
| 5,045,207 A * | 9/1991 | Fecondini et al. .......... 210/645 |
| 5,053,115 A | 10/1991 | Weinberger et al. |
| 5,248,479 A | 9/1993 | Parsons et al. |
| 5,270,166 A | 12/1993 | Parsons et al. |
| 5,451,350 A | 9/1995 | Macho et al. |
| 5,512,131 A | 4/1996 | Kumar et al. |
| 5,585,069 A | 12/1996 | Zanzucchi et al. |

(Continued)

FOREIGN PATENT DOCUMENTS

EP    0110771 A2 *   11/1983

(Continued)

OTHER PUBLICATIONS

Kutter, et al. ("Integrated Microchip Device with Electrokinetically Controlled Solvent Mixing for Isocratic and Gradient Elution in Micellar Electrokinetic Chromatography", Anal. Chem. 1997, 69, 5165-5171).

*Primary Examiner*—Alex Noguerola
(74) *Attorney, Agent, or Firm*—Donald R. McKenna

(57) ABSTRACT

Apparatus and methods for modulating flow rates in microfluidic devices are provided. The methods involve modulating downstream pressure in the device to change the flow rate of materials in an upstream region of the device. Such methods include electrokinetic injection or withdrawal of materials through a side channel and the use of an absorbent material to induce wicking in the channel system. The apparatus provided includes a prefabricated wick in the device to provide for flow rate control. Additional methods for determining velocity of a particle and cell incubation time are also provided.

13 Claims, 14 Drawing Sheets

U.S. PATENT DOCUMENTS

| | | | |
|---|---|---|---|
| 5,699,157 A | 12/1997 | Parce | |
| 5,779,868 A | 7/1998 | Parce et al. | |
| 5,800,690 A | 9/1998 | Chow et al. | |
| 5,842,787 A | 12/1998 | Kopf-Sill et al. | |
| 5,846,727 A | 12/1998 | Soper et al. | |
| 5,852,495 A | 12/1998 | Parce | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 6,416,642 B1 * | 7/2002 | Alajoki et al. | 204/451 |

FOREIGN PATENT DOCUMENTS

| | | |
|---|---|---|
| EP | 0123456 A2 | 1/2000 |
| WO | WO-90-13016 A1 * | 11/1990 |
| WO | WO 96/04547 | 2/1996 |
| WO | WO 98/00231 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 98/00705 | 1/1999 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |

* cited by examiner

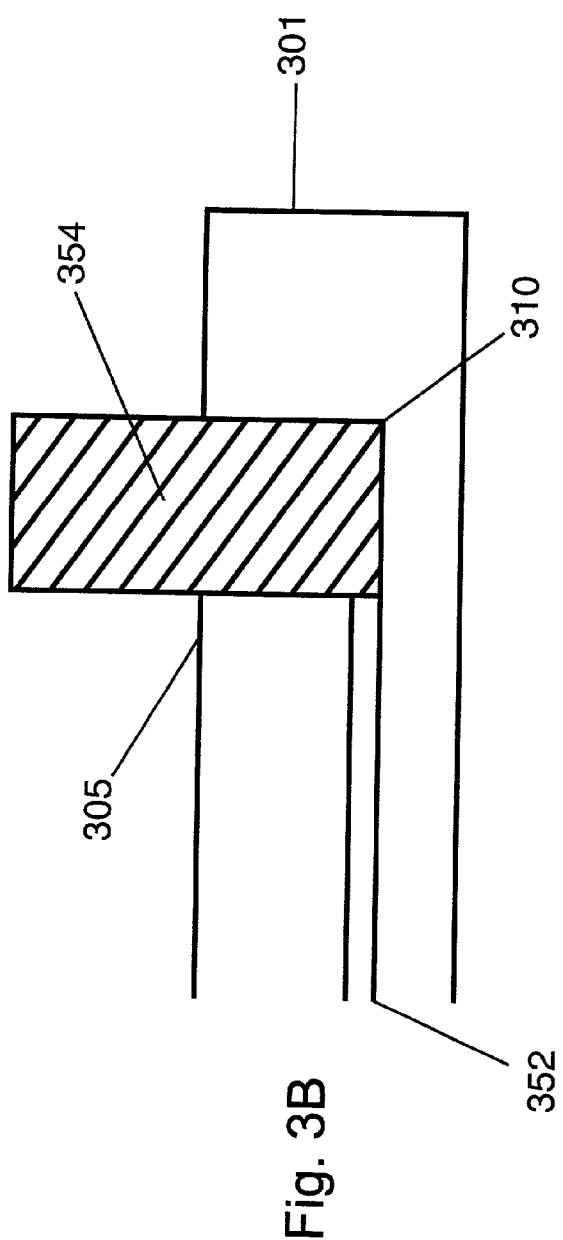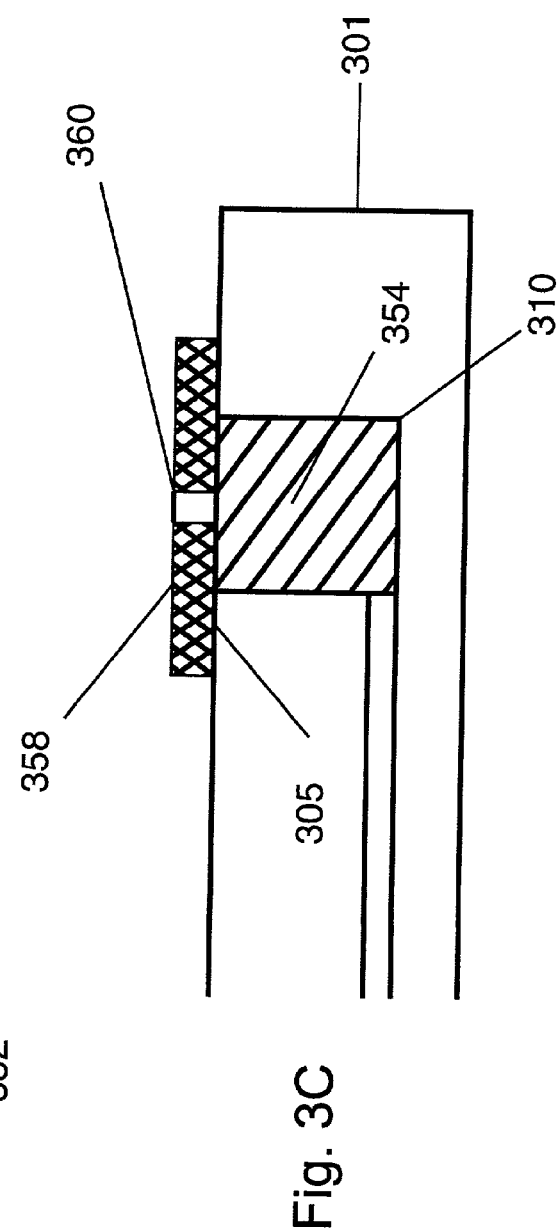
Fig. 3B
Fig. 3C

US 6,989,128 B2

APPARATUS FOR CONTINUOUS LIQUID FLOW IN MICROSCALE CHANNELS USING WICKING

This application is a continuation of U.S. patent application Ser. No. 09/245,627, filed on Feb. 5, 1999, now U.S. Pat. No. 6,416,642, which claims priority from provisional U.S. application Ser. No. 60/116,602, filed Jan. 21, 1999.

BACKGROUND OF THE INVENTION

Microfluidic devices have been designed that are useful in performing high throughput assays useful for biological and chemical screening experiments. Both glass and polymer microfluidic devices comprising microfluidic channels and microfluidic wells are now available. For example, polymer microfluidic devices are provided in PCT application WO 98/46438, "Controlled Fluid Transport in Microfabricated Polymeric Substrates," by Parce et al., and glass devices are set forth in a number of publications and patents set forth herein.

Continuous flow microfluidic systems are set forth in, e.g., published PCT application WO 98/00231, by Parce et al. These devices are useful, for example, in screening large numbers of different compounds for their effects on a variety of chemical and biochemical systems. The devices include a series of channels fabricated on or within the devices. The devices also can include reservoirs, fluidly connected to the channels, that can be used to introduce a number of test compounds into the sample channels and thus perform the assays. Interfacing mechanisms, such as electropipettors, can be incorporated into these high-throughput systems for transporting samples into wells or microfluidic channels. See, e.g., "Electropipettor and Compensation Means for Electrophoretic Bias," U.S. Pat. No. 5,799,868, by Parce et al.

Microfluidic systems for fast, accurate and low cost electrophoretic analysis of materials in the fields of chemistry, biochemistry, biotechnology, molecular biology and numerous other fields, are described in U.S. Pat. No. 5,699,157 by Parce et al. Techniques for transporting materials through microfluidic channels using electrokinetic forces were described in "Electropipettor and Compensation Means for Electrophoretic Bias," U.S. Pat. No. 5,799,868, by Parce et al.

Movement of material through microfluidic channels was further described in "Variable Control of Electroosmotic and/or Electrophoretic Forces within a Fluid Containing Structure Via Electrical Forces," U.S. Pat. No. 5,800,690, by Chow et al. In this patent, various power supplies, such as a time-multiplexed power supplies that vary the voltage on the system, are described that are used to provide control over the fluid movement in a microfluidic device.

Electroosmotic pressure flow has also been described to provide other ways to modulate microfluidic flow rates. For example, these methods can involve providing an effective zwitterionic compound in the fluid containing the material to be transported. See, e.g., Published PCT application, WO 98/45929 by Nikiforov at el. Additionally, Published PCT application, WO 98/56956 by Kopf-Sill et al. provides methods of correcting for variable velocity in microfluidic devices.

Channel dimensions have also been varied to provide further control over the movement of fluid through the channels, such as in "Microfluidic Systems Incorporating Varied Channel Dimensions," See, e.g., U.S. Pat. No. 5,842,787, by Kopf-Sill et al.

Although corrections can be made for variable velocities, see, e.g., Published PCT application, WO 98/56956, by Kopf-Sill et al., it is advantageous to be able to rapidly and easily modulate the velocity or flow rate of a component in a microfluidic device. There exists a need for high throughput screening methods, and associated equipment and devices, that are capable of performing repeated, accurate assay, operating at very small volumes and at regulated and/or continuous flow rates. These assays are particularly useful for high throughput screening, as well as for a variety of research applications.

The present invention meets these and a variety of other needs. In particular, the present invention provides novel methods and apparatuses for performing assays with continuous or discontinuous flow rates, as well as other apparatus methods and integrated systems, which will be apparent upon complete review of the disclosure.

SUMMARY OF THE INVENTION

This invention provides methods, devices and systems for sustaining and/or modulating and/or measuring flow rates in a microfluidic system by modulating pressure downstream from the region or material of interest. In accordance with the invention, flow rates are modulated or regulated to provide continuous or discontinuous flow by a variety of means. For example, an absorbent material such as an absorbent gel, absorbent polymer material or cellulose containing material is optionally placed downstream from the region or material of interest. Alternatively, or additionally, electrokinetic or pressure based injection or withdrawal of materials into or from the system downstream of the material or region of interest may be used to modulate upstream flow rates. For example, a wick (which can be pre-wetted, dry or wetted in position in contact with a microfluidic system) can act by capillary action to draw material through channels or wells in which it is placed in fluidic contact. Alternatively, or additionally, a volume of liquid is optionally injected or withdrawn downstream of the material or region of interest and the flow rate modulated by creating a pressure differential at the site of injection. Microfluidic devices are provided that contain absorbent materials in particular wells or that have particular wells located to serve as microfluidic injection sites.

In one embodiment, the invention provides a method of modulating the flow rate of material in a microfluidic channel system by modulating pressure downstream of the material, thereby increasing or decreasing flow rate of the material in the channel. Pressure modulation is optionally achieved by placing an absorbent material, such as a wick, in a microfluidic well, by electrokinetic injection, by creating a pressure differential, or by a combination of these three methods.

The absorbent material used to modulate pressure in a microfluidic system is placed. e.g., within a well, such as a waste well, or at the junction of a well and a channel. It can extend beyond the top of the well or remain within the well. The absorbent material is, e.g., a solid, porous, gel, or polymeric material. It is optionally, e.g., a high salt fluid, a thermoplastic polymer (e.g., which is porous or sintered) a porous plastic, or a polyolefin resin. Typically, the absorbent material will be a cellulosic material such as a piece of paper, e.g., a Kimwipe, paper towel, cellulose membrane, nylon membrane, Whatman™ filter, blotting paper, filter paper, cloth or fibrous material, or a polymer, such as dried cross-linked polyacrylamide, or a porous or sintered polymer such as a porous or scintered polyethylene, polypropylene, polyvinylidene fluoride, ethylene-vinyl acetate, polytetrafluoroethylene, stryene-acrylonitrile, polysulfone, polycarbonate, or polyhthalate polymer.

The invention also provides a method for modulating flow rate of material in a microfluidic system by electrokinetic injection of a second material downstream of the first material or region of interest. The flow rate is monitored before injection and/or after injection so that it is sustained at a certain level and controlled.

The invention provides methods of monitoring flow rates by detecting a signal from the material in the channel and measuring the duration and amplitude of a signal that is detected by monitoring fluorescence, phosphorescence, radioactivity, pH, or charge.

In another embodiment, the invention provides a method for determining velocity of a particle in a microfluidic channel system by detecting a signal from the particle for a period of time. The signal amplitude corresponds to the number of particles, and the duration corresponds to the velocity of the particle. Once determined, the velocity is optionally modulated or made constant by electrokinetic injection or by use of an absorbent material such as a wick.

In another embodiment, the invention provides for microfluidic devices that contain wicks or other absorbent materials for use in modulating the flow rate of materials in the device. The devices are made to accommodate flow rate control by wicking or other capillary forces, as described above, by electrokinetic injection, pressure differential or a combination of flow rate control elements. A microfluidic system optionally includes a computer and software for simultaneous or sequential monitoring or control over flow rates, as well as analysis.

DEFINITIONS

Figure 1:
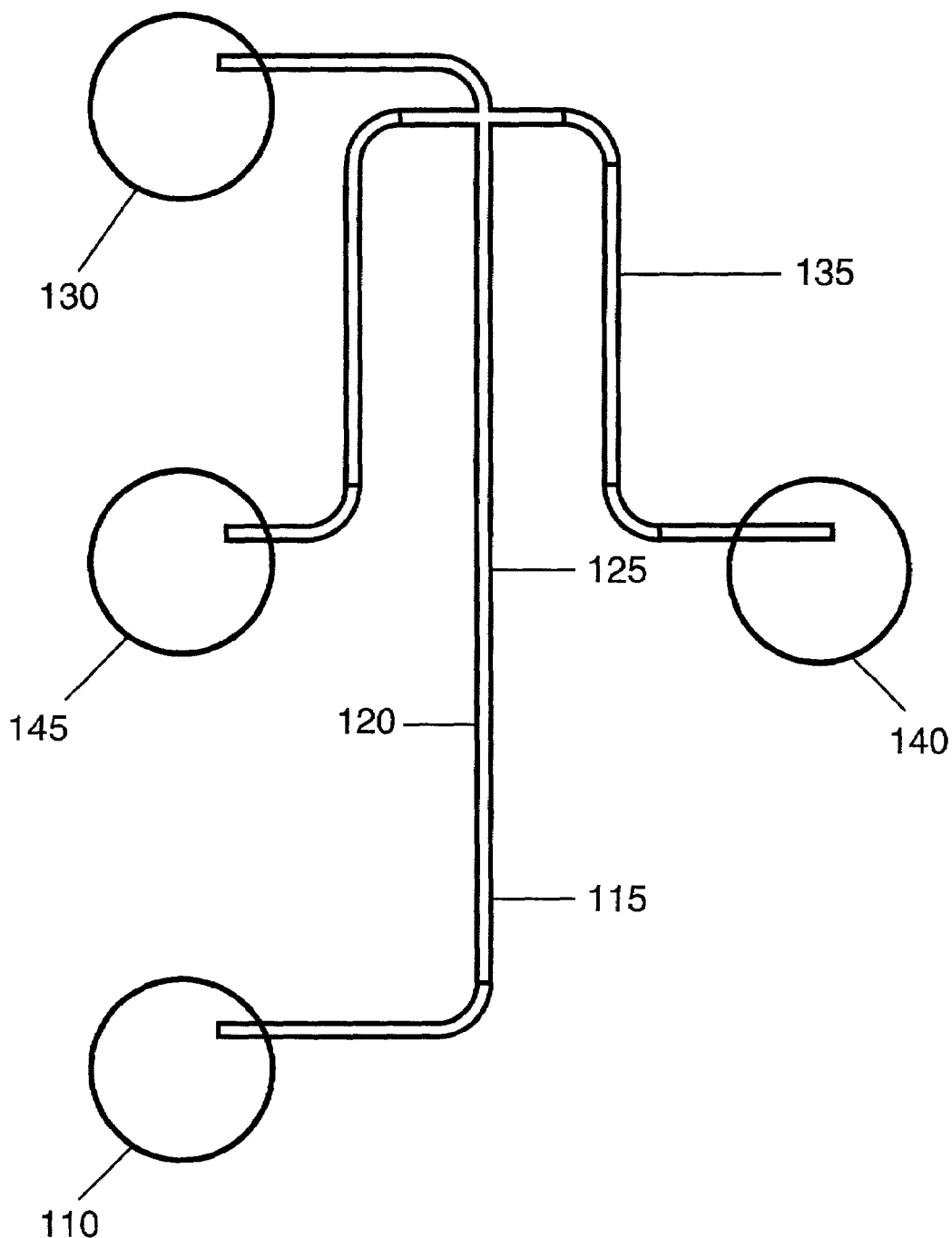
FIG. 1 is a schematic drawing of a microfluidic device of the present invention.

"Microfluidic," as used herein, refers to a system or device having fluidic conduits that are generally fabricated at the micron to submicron scale, e.g., typically having at least one cross-sectional dimension in the range of from about 0.1 $\mu$m to about 500 $\mu$m. The microfluidic system of the invention is fabricated from materials that are compatible with the conditions present in the particular experiment of interest. Such conditions include, but are not limited to, pH, temperature, ionic concentration, pressure, and application of electrical fields. The materials of the device are also chosen for their inertness to components of the experiment to be carried out in the device. Such materials include, but are not limited to, glass, quartz, silicon, and polymeric substrates, e.g., plastics, depending on the intended application.

As used herein, "channel" refers to a fluidic conduit. Channels optionally connect with wells, other channels, or other features of a microfluidic device. The channels are typically of microfluidic dimensions as discussed above.

The term "downstream" refers to a location in a channel that is farther along the channel in a selected direction of fluid or material flow, relative to a selected site or region.

A "well" typically refers to a chamber or reservoir in a microfluidic device or system, e.g., for adding or removing a component to or from the system. The well is optionally open topped or closed within the body of the device. A "waste well" is that chamber to which the results or remains of an experiment are directed. Waste products of an experiment are optionally collected and/or removed from the waste well. A well also optionally functions as a port for providing access to channels, e.g., electrical or fluidic access.

A "wick," as used herein, refers to an absorbent material used to modulate continuous flow in a microfluidic system. Typically, the wick will comprise an absorbent material which absorbs a fluid such as an aqueous or non-aqueous solution. The wick is optionally the same size as the well or other microfluidic element in which it is contained, smaller than the well, larger than the well, extending beyond the upper edge of the well, or in any other configuration.

An "absorbent material" is a substance that has the power or capacity or tendency to absorb or take up fluid. Absorption mechanisms include capillary forces, osmotic forces, solvent or chemical action, or the like. The absorbent material of the invention is optionally a solid material, a porous material, a sintered material, a gel, a polymer, a high salt fluid, a thermoplastic polymer (such as any Porex™ polymer material), a polyolefin resin, or a porous plastic (including, e.g., Porex™ plastics). The absorbent material can be cellulosic material such as paper (e.g., a piece of Kimwipe™, paper towel or the like), but is optionally dried cross-linked polyacrylamide, agarose, or a porous or sintered polymer (e.g., such as a porous or sintered polyethylene, polypropylene, high molecular weight polyethylene, polyvinylidene fluoride, ethylene-vinyl acetate, polytetrafluoroethylene, stryene-acrylonitrile, polysulfone, polycarbonate, dry sephadex, dextran, or polyhthalate), or other materials which will be apparent upon complete review of this disclosure. Additionally, an absorbent material can be a combination of one or more of the above materials.

A "junction" or "intersection" between two channels or between a channel and a well refers to a region in which two or more channels or wells are in fluid communication with each other. The term encompasses "T" intersections, cross intersections, "wagon wheel" intersections of multiple channels and/or wells, or any other channel/well geometry where two or more channels and/or wells are in such fluid communication.

As used herein, the term "thermoplastic polymer" refers to plastics and synthetic resins that are remelted and cooled without undergoing any appreciable chemical changes, such as cellulose acetate and e.g., a variety of pouros or sintered polymers made by Porex Technologies as well as a variety of other commercial sources. See, Porex Technologies catalog, Fairburn, Ga. Other commercial sources include, e.g., Sigma and Aldrich. It includes, but is not limited to, porous or scintered polymers or polymer or plastic particles made from, e.g., ultra high density polyethylene, polypropylene, high molecular weight polyethylene, polyvinylidene fluoride, ethylene-vinyl acetate, polytetrafluoroethylene, stryene-acrylonitrile, polysulfone, polycarbonate, and polyhthalate. A variety of thermoplastic polymers are described in the Kirk-Othmer Encyclopedia of Chemical Technology, $4_{th}$ Edition, Wiley Interscience.

"Porous plastic" refers to a plastic material that is full of holes or pores, or that is capable of absorbing moisture, or which is permeable by liquids. These materials include, but are not limited to, a polyethylene particle, a polypropylene particle, a high molecular weight polyethylene particle, a polyvinylidene fluoride particle, an ethylene-vinyl acetate particle, a polytetrafluoroethylene particle, a stryene-acrylonitrile particle, a polysulfone particle, a polycarbonate particle, and a polyhthalate particle, e.g., such as scintered or plastic beads made by Porex Technologies from polyolefin resins or as available from other commercial sources, such as Sigma and Aldrich.

The functioning of the system is indicated by the production of a detectable event or signal. "Detection" is accomplished by monitoring signals such as optically detectable chromophoric or fluorescent signals that are associated with the functioning of the particular model system used. Other detection systems are described supra, and in cited references.

As used herein, the term "continuous flow" generally refers to an unbroken or contiguous stream of the particular material or composition that is being continuously flowed. For example, a continuous flow of a sample includes a constant or variable fluid flow having a set velocity, or alternatively, a fluid flow which includes pauses in the flow rate of the overall system, such that the pause does not otherwise interrupt the flow stream.

"Velocity" typically refers to the distance a selected component travels (l) divided by the time (t) required for the travel. In many embodiments, the velocity under consideration is essentially constant, e.g., for the travel of reaction components along the length of a microchannel under a constant rate of current in an electrokinetic system or under a constant applied pressure differential. See, e.g., Published PCT application, WO 98/56956, by Kopf-Sill et al. for a discussion of variable velocity in microfluidic systems. Where the velocity changes significantly over time, due, e.g. to change of applied current in an electrokinetic system, or where a change from substrate to product results in a slow acceleration (or deceleration) in the system, an "instantaneous velocity" equal to the change in distance for a selected time ($\Delta l/\Delta t$) can be determined by graphing distance against time and taking the tangent of the resulting function at a particular point in time.

DETAILED DESCRIPTION

Microfluidic devices have been used in biochemical fields to perform high throughput screening assays. One problem in the use of the devices in assays is ensuring a constant and continuous flow rate. Flow in microfludic systems are typically powered by a pressure based system or electrokinetic fluid direction systems. Problems encountered include a cessation or decrease in the flow rate when capillary action is suspended due to evaporation from the waste well or sample material adhering to the corners of the channels. However, for bioassay systems, a constant flow of materials is useful to maintain the assay, ascertain cell incubation time, and reduce time for multiple screening assays. In addition, the ability to modulate flow rates is equally useful in microfluidic systems.

The present invention provides methods for achieving continuous and consistent flow in a microfluidic device by modulation of pressure downstream from any fluid flow that requires regulation as well as, more generally, modulating flow of materials in channels. One way the flow rate is modulated is by positioning an absorbent material in a well or waste well of the device. A wick is one such absorbent material. Devices that contain the elements necessary to perform such regulation are also described in the present invention, e.g., devices that contain wicks.

An alternative or additional way the flow rate is modulated is by electrokinetic or pressure based injection or withdrawal downstream of the channel region containing the sample stream to be modulated.

In addition to providing methods for regulating or modulating flow rates or achieving a continuous flow rate, the invention also provides methods for monitoring and detecting the flow rate in a microfluidic system and measuring the velocity of a particle, such as a bead or cell, in a bioassay carried out in a microfluidic system.

I. Methods of Modulating Flow Rate in a Microfluidic System

The flowing of materials, such as a suspension of cells, through the channels of a microfluidic device is carried out by a number of mechanisms, including pressure based flow, electrokinetic flow, or mechanisms that utilize a hybrid of the two. As noted above, continuous flow is desirable in certain applications, e.g., to modulate or control incubation times. The present invention provides methods of achieving continuous flow and/or regulating or modulating flow rates, e.g., controllably changing the flow rate, in a microfluidic device by modulating the pressure downstream from the sample or material of interest.

A. Sustained Flow is Achieved by Modulating Downstream Pressure

Flow rates through a channel may vary as the assay progresses. For example, material may stick or adhere to the walls of the channel or well and thereby reduce capillary action and/or mask the surface charge for electrokinetic purposes and slow the flow rate of the material through the channel. Alternatively, evaporation from the waste well may concentrate salts in the fluid in the channel, thereby increasing the density and viscosity of the fluid and decreasing the flow rate. In many applications, however, a known and/or constant flow rate is useful, for example, when attempting to establish the incubation time of a cell and a test compound. Furthermore, continuous and/or constant flow facilitates high throughput screening.

Additionally, electrokinetic forces are sometimes avoided to prevent leakage of dyes and non-specific cell responses at high voltages. In these instances, a constant flow is achieved by modulation of the pressure downstream from the sample to be analyzed, for example, by use of a wick.

In these embodiments, a constant flow rate is achieved or to flow regulated by placing an absorbent material in a well channel or reservoir of the microfluidic system. This absorbent material absorbs and draws fluid through the channel. By drawing the fluid up and out of the well, the flow rate stabilizes and is not affected by the adhesion of material to corners, which decreases capillary forces. Likewise, the wick can draw the liquid up before evaporation and thereby avoid concentrating the material and making it denser. The salts of the liquid will likewise be drawn up by the wick along with the fluid material. The wick material, size, shape and placement are optionally varied to achieve the desired flow rate.

Alternatively, the pressure may be regulated by fluid displacement, e.g., using a piston, pressure diaphragm or probe to displace liquid and raise or lower the pressure. An alternate way to modulate the pressure is through a side channel electrokinetic injection or withdrawal (e.g., downstream from the side where flow is modulated), creating a pressure differential by electrokinetically injecting or withdrawing another liquid into or from a side channel and thereby modulating the flow rate. This provides a pressure change downstream of the material of interest, thereby decreasing or increasing the flow rate. This method can also be easily regulated and adjusted as the assay progresses, making it useful for achieving continuous flow, or generally for modulating flow rates.

B. Electrokinetic and Pressure Based Transport Systems

One method of achieving transport or movement of samples through microfluidic channels is by electrokinetic material transport, which forms the basis of the electrokinetic injection or withdrawal methods of the present invention. "Electrokinetic material transport systems," as used herein, includes systems that transport and direct materials within an interconnected channel and/or chamber containing structure, through the application of electrical fields to the materials, thereby causing material movement through and among the channel and/or chambers, i.e., cations will move toward a negative electrode, while anions will move toward a positive electrode.

Such electrokinetic material transport and direction systems include those systems that rely upon the electrophoretic mobility of charged species within the electric field applied to the structure. Such systems are more particularly referred to as electrophoretic material transport systems. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

Other electrokinetic material direction and transport systems rely upon the electroosmotic flow of fluid and material within a channel or chamber structure which results from the application of an electric field across such structures. In brief, when an appropriate fluid is placed in a channel or other fluid conduit having functional groups present at the surface, those groups ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them.

An electrokinetic device moves components by applying an electric field to the components in a microfluidic channel, such as first channel region 115 in FIG. 1. By applying an electric field along the length of the channel, cations will flow toward a negative electrode, while anions will flow towards a positive electrode. Movement of charged species in the fluid pulls the solvent with the fluid, provided the fluid is mobile. In pure electrophoretic applications, elements of the fluid are not mobile, e.g., due to cross-linking, i.e., where the fluid is a gel matrix, or due to a lack of surface charge on the walls of the interior channel.

The steady state velocity of fluid movement is generally given by the equation:

$$v = \frac{\varepsilon \xi E}{4\pi \eta}$$

where v is the solvent velocity, $\epsilon$ is the dielectric constant of the fluid, $\xi$ is the zeta potential of the surface, E is the electric field strength, and $\eta$ is the solvent viscosity. The solvent velocity is, therefore, directly proportional to the surface potential. In this invention, electrokinetic forces are used to modulate the velocity of materials in the channels of a microfluidic device.

To provide appropriate electric fields, the system generally includes a voltage controller that is capable of applying selectable voltage levels, sequentially or, more typically, simultaneously, to each of the reservoirs, including ground. Such a voltage controller is implemented using multiple voltage dividers and multiple relays to obtain the selectable voltage levels. Alternatively, multiple independent voltage sources are used. The voltage controller is electrically connected to each of the reservoirs via an electrode positioned or fabricated within each of the plurality of reservoirs. In one embodiment, multiple electrodes are positioned to provide for switching of the electric field direction in a microchannel, thereby causing the analytes to travel a longer distance than the physical length of the microchannel. Use of electrokinetic transport to control material movement in interconnected channel structures was described, e.g., in WO 96/04547 to Ramsey, which is incorporated by reference.

Modulating voltages are concomitantly applied to the various reservoirs to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various reservoirs can move and direct fluid flow through the interconnected channel structure of the device.

Some biological cell assays useful in the present invention do not work well in an electrically controlled system because high voltages may cause an undesired cellular response. Another way to control flow rates is through creation of a pressure differential. For example, in a simple passive aspect, a cell suspension is deposited in a reservoir or well at one end of the channel, and at sufficient volume or depth, that the cell suspension creates a hydrostatic pressure differential along the length of the channel, e.g., by virtue of its having greater depth than a well at an opposite terminus of the channel. Typically, the reservoir volume is quite large in comparison to the volume or flow through rate of the channel, i.e., 10 μl reservoirs or larger as compared to a 100 μm channel cross section. Another pressure based system is one that displaces fluid in a microfluidic channel using, e.g., a Alternatively, a pressure differential is applied across the length of the channel. For example, a pressure source is optionally applied to one end of the channel, and the applied pressure forces the material through the channel. For example, in FIG. 1, a pressure applied at main injection well 110 or first channel region 115 would force a cell suspension through reading area 120, second channel region 125, and into waste well 130. The pressure is optionally pneumatic, e.g., a pressurized gas or liquid, or alternatively a positive displacement mechanism, i.e., a plunger fitted into a material reservoir, for forcing the material along through the channel. Pressure can, of course, also be due to electrokinetic force.

Alternatively, a vacuum source (i.e., a negative pressure source) is applied to a reservoir or well at the opposite end of the channel to draw the suspension through the channel. In FIG. 1, a vacuum source placed in waste well 130 draws a cell suspension from, e.g., main injection well 110, or from buffer well 145 or from reading area 120. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

In screening applications, varying the flow rate of a cell suspension is optionally used, e.g., to vary the incubation time of the cells with a test compound (e.g., potential inhibitor, activator, ligand or the like). In particular, by slowing the flow rate of cells along the channel, one can effectively lengthen the amount of time between introduction of a test compound and detection of its effects. Channel lengths, detection points, or test compound introduction points are varied in the fabrication of the microfluidic device to vary incubation times. However, this invention provides easier and more flexible ways to vary and regulate the flow rate in a channel, thereby providing better ways to monitor and control cell incubation time. The pressure based elements and electrokinetic transport systems discussed above are used with this invention to provide continuous flow rates.

II. Using a Wick or Other Absorbent Material in a Microfluidic Device to Control the Flow Rate A. Wick/Absorbent Materials A wick is an absorbent material used to modulate and sustain flow rates of a sample in a microfluidic system. Typically the wick will comprise an absorbent material, i.e., a substance that has the power, capacity or tendency to absorb or take up fluid. Absorption mechanisms include capillary forces, osmotic forces, solvent or chemical action or the like.

Absorbent materials of the invention include solid materials, porous materials, gels, porous or sintered polymers, high salt fluids, thermoplastic polymers (such as those available from Sigma, Aldrich, Porex™, etc.), polyolefin resins, or porous plastics, including, e.g., Porex™ plastics.

The absorbent wick material is optionally a cellulosic material such as paper, e.g., Kimwipe™, paper towel or the like. The absorbent material can also be, e.g., dried polyacrylamide, polyethylene, polypropylene, a high molecular weight polyethylene, polyvinylidene fluoride, ethylene-vinyl acetate, polytetrafluoroethylene, stryene-acrylonitrile, polysulfone, polycarbonate, dextran, dry sephadex, or polyhthalate, or other materials which will be apparent upon complete review of this disclosure. The absorbent material can be wetted prior to being placed into contact with the microfluidic device, or can be dry prior to placement in contact with a microfluidic device. Pre-wetting can aid in establishing capillary flow for some materials, but is not typically required. For example, one can fill a device with buffer, add samples and e.g., cells or other biological materials, apply a wick or other absorbent material in fluid communication with fluid in the device, and even reduce evaporative effects by applying a cap to the wick to prevent evaporation. One of skill can easily assess the desirablity of pre-wetting by varying the wetting strategy and observing any resulting alteration in flow properties.

The absorbent wick material is optionally a disposable or reusable material, such as a piece of Kimwipe™, or other absorbent cellulosic material, or, e.g. a porous plastic plug that fits into a micro well, or the like. Additionally, the absorbent material may take on a variety of shapes. It is optionally a narrow rectangular piece of absorbent material that extends beyond the upper edge of a well or into the channel or a rounded piece of absorbent material that sits inside the well. More of the absorbent material is optionally situated above the fluid surface than below or the reverse, depending on the flow rate one wants to achieve. Alternatively, the wick is optionally a solid plug of absorbent material that fits snugly or loosely in a well or reservoir (or channel). It can also be a porous plastic tube that extends into a channel or extends beyond the top of the well or reservoir in which it is located. Almost any shape imaginable is optionally used as a "wick" and its effect on the flow rate is easily determined. For example, the flow rate is optionally determined by monitoring the amount of labeled or otherwise detectable material passing the detection window, e.g., using a microscope. For example, using this monitoring technique, it was determined that a narrow wick provides a slower flow rate than a wide wick.

The wick or other absorbent material used optionally includes a surfactant to assist the wicking process. Surfactants can be obtained from any of a variety of sources, such as the SIGMA chemical company (Saint Louis, MO). The absorbent material of the present invention is optionally soaked in a surfactant prior to use or before, during or after fabrication. For example, such surfactant impregnated materials include, but are not limited to, the products manufactured by Filtrona Richmond Inc., Richmond, Va.

B. Location of the Wick and Use of the Wick Within the Microfluidic System

A wick is optionally used in a microfluidic device by positioning it in a well, such as a waste well, or at the junction between a well and a channel. The wick need only be placed at a location that allows it to take up fluid and pull the material or sample stream toward it.

The wick is optionally internal or external to the microfluidic device or system. For example, the wick is optionally placed entirely within a well or channel of a microfluidic system, or it can extend out from the top of a well or reservoir. Furthermore, the wick is optionally the same size as the well in which it is contained, smaller than the well, or larger than the well, in which case it may extend beyond the top of the well.

In one embodiment, a wick is used in a microfluidic channel by first filling the channels with a liquid and designating an empty well as the "waste well". A piece of absorbent material is sized to fit at least partially in the well (or, e.g., a capillary can extend from the well to the wick). The wick is placed into the well and optionally wetted with liquid to help begin the wicking action by drawing the liquid up and out of the well (generally, the absorbent material can be pre-wetted (i.e., wetted prior to contact with the fluid, reservoir or channel at issue) to facilitate or regulate osmotic pressure and, therefore, wicking action. Furthermore, by placing a wick in one well, the entire system of channels or any subset thereof is optionally regulated by fluidly connecting all or some channels to the well containing the wick.

C. Devices and Systems That Contain Wicks

In other embodiments, the wick is a disposable or re-usable cellulosic material, e.g., piece of paper, membrane, filter, fabric, or other fibrous material that is replaced after each use of the wick. In an alternate embodiment, it is a reusable piece of porous plastic that is placed in fluidic contact with a fluidic channel in the microfluidic system. Microfluidic devices and systems are fabricated, as described in, e.g., U.S. Pat. No. 5,842,787, titled "Microfluidic Systems Incorporating Varied Channel Dimensions," by Kopf-Sill et al., or in the other references herein, with an absorbent material or wick being fabricated into a well of the device. The wick is positioned in the well or at the junction between a well and a channel. The wicks placed into fabricated devices are made from the materials, used and positioned as described above. The wicks or other absorbent materials are optionally manufactured and/or sold separately and fitted into the well or wells of prefabricated microfluidic devices. An alternative way to fabricate a microfluidic device with a wick is to use an absorbent material that is sprayed into the well, such as an aerosol particulate spray (e.g., comprising porous particulate matter).

III. Electrokinetic Injection or Withdrawal to Modulate the Flow Rate in a Microfluidic System In the event that the absorbent material does not provide the flow rate desired, an additional or substitute method of modulation is optionally used. Electrokinetic material transport, as described above, is optionally used to inject fluids or other materials into the region of interest in a microfluidic channel. Electrokinetic injection of materials into a microfluidic device is accomplished by providing a voltage gradient between the source of test materials, i.e., a well or reservoir, and the intersecting channel structure in the interior of the device. The voltage is applied such that the material flows from the well into a channel or from a channel into a well. This voltage is optionally applied by a power source, for example, via electrodes. Furthermore, this method can be applied in conjunction with the wick method described above to provide a full range of continuous flow rates.

Upstream flow modulation is achieved by decreasing the upstream flow rate, e.g., by flowing liquid into the channel downstream or increasing the upstream flow rate by drawing liquid out of the channel downstream of the region of interest. Changing the channel geometry, for example by increasing or decreasing channel width, or by etching a network of capillaries downstream of a selected channel region serves a similar function, but this is not conveniently changed once the device has been fabricated, and does not offer the same flexibility as electrokinetic or pressure based injection. Nevertheless, the use of selected channel geometries, e.g., for performing repetitive assays is also useful. For example, etching a plurality of capillary channels downstream of a selected channel region (typically during device manufacture), where the plurality of channel regions are, during use of the apparatus, in fluidic communication with the selected channel region, also finds use in the present invention.

Fluidic injection provides flexibility because injection rates can be adjusted as the need for modulation arises or changes, while a change of channel geometry is typically permanent once the device has been fabricated. Electrokinetic injection provides an adjustable flow rate control by moving liquid into the main channel through a side-channel injection, e.g., through the application of an appropriate current between the side channel and main channel. The higher the side channel injection rate, the slower the material (e.g., cell) movement upstream of the injection site. When the side channel injection is turned off or decreased, the material flow rate upstream of the injection site increases. Alternatively, the polarity of the electrokinetic injection can be reversed to increase the flow rate in the main channel by pulling fluid out of the main channel into the side channel.

Furthermore, because injection is optionally performed in a side channel downstream of the detection window, the buffer used does not necessarily sample contact materials such as cells in an assay in the main channel until after the results of the assay have been measured. Therefore, the velocity of materials is controlled without moving parts and the pumped buffer can be optimized for pumping efficiency, since it will not affect the materials in the assay.

In another embodiment, the two above methods of flow modulation are combined. For example, a wick is used to provide sustained flow at a high rate and if a slower rate is needed the electrokinetic injection method is used to slow the rate down to a desired level. An added advantage is that both are easily and readily adjusted to suit the needs of the assay of interest.

IV. Methods for the Monitoring of Flow Rate in a Microfluidic Device and the Detection of Bioassay Signals This invention provides methods of monitoring samples in a microfluidic device. First, a sample must be introduced (e.g., injected, flowed or placed) into the device. Typically, samples are injected into a channel, well or reservoir, for example, using a micro-pipettor or electropipettor. Once injected, the sample is transported through the channels of the device and modulated by one of the methods described above, such as electrokinetic forces, pressure based elements, wicks, or combinations thereof.

Once a sample has been introduced into the device and is being transported through the channel or channels of the device, the flow rate of the sample and the velocity of a particle in the sample, such as a cell, are measured. To monitor the sample and measure the flow rate or velocity, first the sample or sample components are detected. Detection typically occurs through the use of a label associated with the material of interest. A "label" is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands are optionally used. Where a ligand has a natural anti-ligand, for example, biotin, thyroxine, or cortisol, it is used in conjunction with the labeled, naturally occurring anti-ligands. Alternatively, any haptenic or antigenic compound can be used in combination with an antibody (see, e.g., Coligan (1991) *Current Protocols in Immunology* Wiley/Greene, N.Y.; and Harlow and Lane (1989) *Antibodies: A Laboratory Manual* Cold Spring Harbor Press, N.Y. for a general discussion of how to and use antibodies). The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include, e.g., luciferin, and 2,3-dihydrophthalazinediones, e.g., luminol.

In some embodiments, a first and second label on the same or different components interact when in proximity (e.g., due to fluorescence resonance energy transfer or "FRET"), and the relative proximity of the first and second labels is determined by measuring a change in the intrinsic fluorescence of the first or second label. For example, the emission of a first label is sometimes quenched by proximity of the second label. This technique is particularly suited for measurement of binding reactions, protein-protein interactions and other biological events altering the proximity of two labeled molecules. Many appropriate interactive labels are known. For example, fluorescent labels, dyes, enzymatic labels, and antibody labels are all appropriate. Examples of interactive fluorescent label pairs include terbium chelate and TRITC (tetrarhodamine isothiocyanate), europium cryptate and Allophycocyanin, DABCYL and EDANS and many others known to one of skill. Similarly, two colorimetric labels can result in combinations which yield a third color, e.g., a blue emission in proximity to a yellow emission provides an observed green emission. With regard to preferred fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of nonfluorescent ground state species. Self quenching is the quenching of one fluorophore by another; it tends to occur when high concentrations, labeling densities, or proximity of labels occurs. FRET is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (996) *Handbook of Fluorescent Probes and Research Chemicals* Published by Molecular Probes, Inc., Eugene, Oreg. e.g., at chapter 13).

Detectors for detecting the labeled compounds of the invention are known to those of skill in the art. Thus, for example, where the label is a radioactive label, means for detection include a scintillation counter or photographic film as in autoradiography. Where the label is a fluorescent label, it is detected by exciting the fluorochrome with the appropriate wavelength of light and detecting the resulting fluorescence. The fluorescence is optionally detected visually, by means of photographic film, by the use of electronic detectors such as charge coupled devices (CCDs) or photomultipliers, phototubes, photodiodes or the like. Similarly, enzymatic labels are detected by providing the appropriate substrates for the enzyme and detecting the resulting reaction product. Finally simple colorimetric labels are detected simply by observing the color associated with the label. This is done using a spectrographic device, e.g., having an appropriate grating, filter or the like allowing passage of a particular wavelength of light, and a photodiode, or other detector for converting light to an electronic signal, or for enhancing visual detection.

The microfluidic device includes a detection window or zone at which a signal is monitored. For example, reactants or assay components are contacted in a microfluidic channel in first region 115, and subsequently flowed into reading area 120, comprising a detection window or region. The first and second channel region are optionally part of a single channel, but can also be separate channels, e.g., which are in fluid connection. This detection window or region typically includes a light or radiation transparent cover allowing visual or optical observation and detection of the assay results, e.g., observation of a colorometric, fluorometric or radioactive response, or a change in the velocity of colorometric, fluorometric or radioactive component. Detectors detect a labeled compound. Example detectors include spectrophotometers, photodiodes, microscopes, scintillation counters, cameras, film and the like, as well as combinations thereof. Examples of suitable detectors are widely available from a variety of commercial sources known to persons of skill.

In one aspect, monitoring of the signals at the detection window is achieved using an optical detection system. For example, fluorescence based signals are typically monitored using, e.g., in laser activated fluorescence detection systems which employ a laser light source at an appropriate wavelength for activating the fluorescent indicator within the system. Fluorescence is then detected using an appropriate detector element, e.g., a photomultiplier tube (PMT). Similarly, for screens employing colorometric signals, spectrophotometric detection systems are employed which detect a light source at the sample and provide a measurement of absorbance or transmissivity of the sample. See also, *The Photonics Design and Applications Handbook*, books 1, 2, 3 and 4, published annually by Laurin Publishing Co., Berkshire Common, P.O. Box 1146, Pittsfield, Mass. for common sources for optical components.

In alternative aspects, the detection system comprises non-optical detectors or sensors for detecting a particular characteristic of the system disposed within the detection window. Such sensors may include temperature (useful, e.g. when a reaction produces or absorbs heat), conductivity, potentiometric (pH, ions), amperometric (for compounds that are oxidized or reduced, e.g., $O_2$, $H_2O_2$, $I_2$, oxidizable/reducible organic compounds, and the like).

Alternatively, schemes similar to those employed for the enzymatic system are optionally employed, where there is a signal that reflects the interaction of the receptor with its ligand. For example, pH indicators which indicate pH effects of receptor-ligand binding are optionally incorporated into the device along with the biochemical system, i.e., in the form of encapsulated cells, whereby slight pH changes resulting from binding are detected. See Weaver, et al., *Bio/Technology* (1988) 6:1084–1089. Additionally, one can monitor activation of enzymes resulting from receptor ligand binding, e.g., activation of kinases, or detect conformational changes in such enzymes upon activation, e.g., through incorporation of a fluorophore which is activated or quenched by the conformational change to the enzyme upon activation.

One conventional system carries light from a specimen field to a cooled charge-coupled device (CCD) camera. A CCD camera includes an array of picture elements (pixels). The light from the specimen is imaged on the CCD. Particular pixels corresponding to regions of the substrate are sampled to obtain light intensity readings for each position. Multiple positions are processed in parallel and the time required for inquiring as to the intensity of light from each position is reduced. Many other suitable detection systems are known to one of skill.

Once the sample or its components are detected, the flow rate is optionally monitored by measuring the amplitude and duration of the detection signal. The flow rate of the materials being assayed is then determined. In one aspect, the number of cells being measured is determined by the amplitude of the signal and the flow rate is determined by the duration of the signal for single cells. For example, the flow rate equals the length of the detection window or reading frame divided by the duration of the signal; thus, a longer signal duration corresponds to a slower flow rate.

V. Determination of Velocity

The velocity of a particle is optionally determined using the methods of the invention. When a particle, such as a cell in a cell assay is injected into a microfluidic system as described below, its velocity is optionally determined and modulated by the methods described above. While the discussion below is specific for cells for purposes of illustration, one of skill will recognize that other components, e.g., particles, including labeled and unlabled particles can be used in similar fashion.

To determine the velocity of a cell, for example, the cell suspension is injected into main injection well 110 and transported through the channel system by any of a variety of methods, such as pressure differential methods, e.g., applied pressure, wicking, hydrostatic pressure or the like, or electrokinetic methods, both with and without downstream modulation as discussed above.

The cell is then detected in a detection window as described above. As the cell flows through the detection window, signal due to fluorescence, for example, is detected and measured. The signal has an amplitude and duration which are measured, for example, by a computer operably linked to the detector. The amplitude of the signal correlates to the number of cells in the window at the time of detection. The duration of the signal corresponds to how long the cell was in the window and thus the velocity is determined by how long the cell took to traverse the detection window. Single cells traversing the detection window are preferred for use in measuring velocity.

After this determination, one can determine the incubation time of the cell with a test reagent. With a known velocity, the time the cell spent in contact with a reagent is optionally determined from the time if injection or mixing of the cell with the reagent in the channels. Then using the methods of modulation as described above, this incubation time can be adjusted to suit the particular needs of the system being studied. For example, increasing downstream pressure, e.g., via electrokinetic injection, slows upstream velocity and thereby results in a longer incubation time, while decreasing downstream pressure, e.g., by electrokinetic withdrawal, increases upstream velocity and thereby results in a shorter incubation time.

VI. Example Bioassays Which Can Be Adapted to the Devices of the Invention

The present invention provides novel microlaboratory systems and methods that are useful for performing high-throughput screening assays. In particular, the present invention provides microfluidic devices and methods of using such devices for screening large numbers of different compounds for their effects on a variety of chemical and biochemical systems. Methods of controlling, modulating and/or determining the flow rate in these systems are also provided.

As used herein, the phrase "biochemical system" generally refers to a chemical interaction that involves molecules of the type generally found within living organisms. Such interactions include the full range of catabolic and anabolic reactions which occur in living systems including enzymatic, binding, signalling and other reactions. Further, biochemical systems, as defined herein, also include model systems which are mimetic of a particular biochemical interaction. Examples of biochemical systems of particular interest in practicing the present invention include, e.g., receptor-ligand interactions, enzyme-substrate interactions, cellular signaling pathways, transport reactions involving model barrier systems (e.g., cells or membrane fractions) for bioavailability screening, and a variety of other general systems. Cellular or organismal viability or activity may also be screened using the methods and apparatuses of the present invention, e.g., in toxicology studies. Biological materials which are assayed include, but are not limited to, cells, cellular fractions (membranes, cytosol preparations, mitochondria, nuclei, etc.), agonists and antagonists of cell membrane receptors (e.g., cell receptor-ligand interactions such as e.g., transferrin, c-kit, viral receptor ligands (e.g., CD4-HIV), cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook* Academic Press New York and Hulme (ed) *Receptor Ligand Interactions A Practical Approach* Rickwood and Hames (series editors) IRL Press at Oxford Press N.Y.), toxins and venoms, viral epitopes, hormones (e.g., opiates, steroids, etc.), intracellular receptors (e.g.

which mediate the effects of various small ligands, including steroids, thyroid hormone, retinoids and vitamin D; for reviews see, e.g. Evans (1988) *Science*, 240:889–895; Ham and Parker (1989) *Curr. Opin. Cell Biol.*, 1:503–511; Burnstein et al. (1989), *Ann. Rev. Physiol.*, 51:683–699; Truss and Beato (1993) *Endocr. Rev.*, 14:459–479), peptides, r enzymes, enzyme substrates, cofactors, drugs, lectins, sugars, nucleic acids (both linear and cyclic polymer configurations), oligosaccharides, proteins, phospho-lipids and antibodies. Synthetic polymers such as hetero-polymers in which a known drug is covalently bound to any of the above, such as poly-urethanes, polyesters, polycarbonates, polyureas, polyamides, polyethyleneimines, polyarylene sulfides, polysiloxanes, polyimides, and polyacetates are also assayed. Other polymers are also assayed using the systems described herein, as would be apparent to one of skill upon review of this disclosure. One of skill will be generally familiar with the biological literature. For a general introduction to biological systems, see, Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); *Current Protocols in Molecular Biology*, F. M. Ausubel et al., eds., Current Protocols, a joint venture between Greene Publishing Associates, Inc. and John Wiley & Sons, Inc., (through 1997 Supplement) (Ausubel); Watson et al (1987) *Molecular Biology of the Gene, Fourth Edition* The Benjamin/Cummings Publishing Co., Menlo Park, Calif.; Watson et al (1992) Recombinant DNA Second Edition Scientific American Books, N.Y.; Alberts et al. (1989) *Molecular Biology of the Cell Second Edition* Garland Publishing, N.Y.; Pattison (1994) *Principles and Practice of Clinical Virology;* Darnell et al., (1990) *Molecular Cell Biol Freeman and Company;* Berkow (ed.) *The Merck Manual of Diagnosis and Therapy*, Merck & Co., Rahway, N.J.; *Harrison's Principles of Internal Medicine*, Thirteenth Edition, Isselbacher et al. (eds). (1994) Lewin *Genes,* 5th Ed., Oxford University Press (1994); The "Practical Approach" Series of Books (Rickwood and Hames (series eds.) by IRL Press at Oxford University Press, N.Y.; The "FactsBook Series" of books from Academic Press, N.Y., ; Product information from manufacturers of biological reagents and experimental equipment also provide information useful in assaying biological systems. Such manufacturers include, e.g., the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

In order to provide methods and devices for screening compounds for effects on biochemical systems, the present invention generally incorporates models of in vitro systems which mimic a given biochemical system in vivo for which effector compounds are desired. To provided a system that mimics a biochemical system, it is often useful to have a controlled flow rate to modulate, for example, a cell incubation period. Additionally, the ability to measure the velocity of the components in the system is a great advantage to the ability to modulate and control the system. These methods are provided in the present invention. The range of systems against which compounds can be screened and for which effector compounds are desired, is extensive. For example, compounds are optionally screened for effects in blocking, slowing or otherwise inhibiting key events associated with biochemical systems whose effect is undesirable. For example, test compounds are optionally screened for their ability to block systems that are responsible, at least in part, for the onset of disease or for the occurrence of particular symptoms of diseases, including, e.g., hereditary diseases, cancer, bacterial or viral infections and the like. To perform screening for large numbers of test compounds, a microfluidic device that provides continuous flow as those of the invention, is a great advantage because the testing can be carried out non-stop and with no added time for flow rate adjustments. The invention also provides method of monitoring the flow rates so that the adjustments can be quickly and easily determined and made. Compounds which slow promising results in these screening assay methods can then be subjected to further testing to identify effective pharmacological agents for the treatment of disease or symptoms of a disease.

Alternatively, compounds can be screened for their ability to stimulate, enhance or otherwise induce biochemical systems whose function is believed to be desirable, e.g., to remedy existing deficiencies in a patent.

Once a model system is selected, batteries of test compounds can then be applied against these model systems. By identifying those test compounds that have an effect on the particular biochemical system, in vitro, one can identify potential effectors of that system, in vivo.

In their simplest forms, the biochemical system models employed in the methods and apparatuses of the present invention will screen for an effect of a test compound on an interaction between two components of a biochemical system, e.g., receptor-ligand interaction, enzyme-substrate interaction, and the like. In this form, the biochemical system model will typically include the two normally interacting components of the system for which an effector is sought, e.g., the receptor and its ligand or the enzyme and its substrate. With the methods provided herein, the length of time of the interaction is conveniently determined and modulated if necessary.

Determining whether a test compound has an effect on this interaction then involves contacting the system with the test compound and assaying for the functioning of the system, e.g., receptor-ligand binding or substrate turnover. The assayed function is then compared to a control, e.g., the same reaction in the absence of the test compound or in the presence of a known effector. Typically, such assays involve the measurement of a parameter of the biochemical system. By "parameter of the biochemical system" is meant some measurable evidence of the system's functioning, e.g., the presence or absence of a labeled group or a change in molecular weight (e.g., in binding reactions, transport screens), the presence or absence of a reaction product or substrate (in substrate turnover measurements), or an alteration in electrophoretic mobility (typically detected by a change in elution time of a labeled compound).

Although described in terms of two-component biochemical systems, the methods and apparatuses may also be used to screen for effectors of much more complex systems, where the result or end product of the system is known and assayable at some level, e.g., enzymatic pathways, cell signaling pathways and the like. Alternatively, the methods and apparatuses described herein are optionally used to screen for compounds that interact with a single component of a biochemical system, e.g., compounds that specifically bind to a particular biochemical compound, e.g., a receptor, ligand, enzyme, nucleic acid, structural macromolecule, etc.

Biochemical system models may also be embodied in whole cell systems. For example, where one is seeking to screen test compounds for an effect on a cellular response, whole cells are optionally utilized. Modified cell systems may also be employed in the screening systems encompassed herein. For example, chimeric reporter systems are optionally employed as indicators of an effect of a test compound on a particular biochemical system. Chimeric reporter systems typically incorporate a heterogenous reporter system integrated into a signaling pathway which signals the binding of a receptor to its ligand. For example, a receptor is fused to a heterologous protein, e.g., an enzyme whose activity is readily assayable. Activation of the receptor by ligand binding then activates the heterologous protein which then allows for detection. Thus, the surrogate reporter system produces an event or signal which is readily detectable, thereby providing an assay for receptor/ligand binding. Examples of such chimeric reporter systems have been previously described in the art.

Additionally, where one is screening for bioavailability, e.g., transport, biological barriers are optionally included. The term "biological barriers" generally refers to cellular or membranous layers within biological systems, or synthetic models thereof. Examples of such biological barriers include the epithelial and endothelial layers, e.g. vascular endothelia and the like.

Biological responses are often triggered and/or controlled by the binding of a receptor to its ligand. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Another example is the G-protein coupled receptor class of receptors that are triggered by a wide variety of peptide and small molecule agonists, activating the $G\alpha$ and $G\beta\gamma$ G-protein subunits that have numerous cellular effects controlled through signal transduction pathways and second messenger modulation. Accordingly, control of the interaction of the receptor and its ligand may offer control of the biological responses caused by that interaction.

Accordingly, in one aspect, the present invention will be useful in screening for compounds that affect an interaction between a receptor molecule and its ligands. As used herein, the term "receptor" generally refers to one member of a pair of compounds which specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs may also include antibody/antigen binding pairs, complementary nucleic acids, nucleic acid associating proteins and their nucleic acid ligands. A large number of specifically associating biochemical compounds are well known in the art and can be utilized in practicing the present invention.

Traditionally, methods for screening for effectors of a receptor/ligand interaction have involved incubating a receptor/ligand binding pair in the presence of a test compound. The level of binding of the receptor/ligand pair is then compared to negative and/or positive controls. Where a decrease in normal binding is seen, the test compound is determined to be an inhibitor of the receptor/ligand binding. Where an increase in that binding is seen, the test compound is determined to be an enhancer or inducer of the interaction.

A similar, and perhaps overlapping, set of biochemical systems includes the interactions between enzymes and their substrates. The term "enzyme" as used herein, generally refers to a protein which acts as a catalyst to induce a chemical change in other compounds or "substrates."

Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is them compared to a control, i.e., enzyme contacted with substrate in the absence of test compound or presence of a known effector. As above, a compound that reduces the enzymes activity toward its substrate is termed an "inhibitor," whereas a compound that accentuates that activity is termed an "inducer."

Generally, the various screening methods encompassed by the present invention involve the serial introduction of a plurality of test compounds into a microfluidic device. Once injected into the device, the test compound is screened for effect on a biological system using a continuous serial or parallel assay orientation.

As used herein, the term "test compound" refers to the collection of compounds that are to be screened for their ability to affect a particular biochemical system. Test compounds may include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the test compounds are provided, e.g., injected into a microfluidic device, free in solution, or are optionally attached to a carrier, or a solid support, e.g., beads. A number of suitable solid supports are employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds are screened individually, or in groups. Group screening is particularly useful where hit rates for effective test compounds are expected to be low such that one would not expect more than one positive result for a given group. Alternatively, such group screening is used where the effects of different test compounds are differentially detected in a single system, e.g., through electrophoretic separation of the effects, or differential labeling which enables separate detection.

Test compounds are commercially available, or derived from any of a variety of biological sources apparent to one of skill and as described, supra. In one aspect, a tissue homogenate or blood sample from a patient is tested in the assay systems of the invention. For example, in one aspect, blood is tested for the presence or activity of a biologically relevant molecule. For example, the presence and activity level of an enzyme are detected by supplying and enzyme substrate to the biological sample and detecting the formation of a product using an assay systems of the invention. Similarly, the presence of infectious pathogens (viruses, bacteria, fungi, or the like) or cancerous tumors can be tested by monitoring binding of a labeled ligand to the pathogen or tumor cells, or a component of the pathogen or tumor such as a protein, cell membrane, cell extract or the like, or alternatively, by monitoring the presence of an antibody against the pathogen or tumor in the patient's blood. For example, the binding of an antibody from a patient's blood to a viral protein such as an HIV protein is a common test for monitoring patient exposure to the virus. Many assays for detecting pathogen infection are well known, and are adapted to the assay systems of the present invention.

Biological samples are derived from patients using well known techniques such as venipuncture or tissue biopsy. Where the biological material is derived from non-human animals, such as commercially relevant livestock, blood and tissue samples are conveniently obtained from livestock processing plants. Similarly, plant material used in the assays of the invention are conveniently derived from agricultural or horticultural sources. Alternatively, a biological sample can be from a cell or blood bank where tissue and/or blood are stored, or from an in vitro source such as a culture of cells. Techniques and methods for establishing a culture of cells for use as a source for biological materials are well known to those of skill in the art. Freshney *Culture of Animal Cells a Manual of Basic Technique, Third Edition* Wiley-Liss, New York (1994) provides a general introduction to cell culture.

Any of the above assays or screens are optionally performed in the systems of the invention. When a particular flow rate is desired, the methods of the invention are used to modulate the downstream pressure to provide a particular flow rate. The velocity of the materials in the assay is optionally measured by the methods of the present invention. The velocity and/or incubation time of a cell is then optionally controlled or modulated by the techniques described above, such as by use of a wick or electrokinetic injection. Using these methods, the assays are optionally run continuously and consistently at desired flow rates.

VII. Description of Microfluidic Devices and Systems

The wick and electrokinetic injections of the invention are typically used to run bioassays of the type described above in the microfluidic devices and systems described below. To provide continuous and consistent flow in the bioassays, the microfluidic devices below are optionally fitted with an absorbent material fabricated into a well, such as Porex™ plug fitted into a waste well of the device, or a well is provided for later insertion of a wick or other absorbent material, such as piece of paper. The absorbent material is provided to modulate or control the flow rate of materials within the device.

As used herein, the term "microscale" or "microfabricated" generally refers to structural elements or features of a device which have at least one fabricated dimension in the range of from about $0.1\mu$ to about $500\mu$. Thus, a device referred to as being microfabricated or microscale will include at least one structural element or feature, such as a channel, well, or absorbent wick, having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than $500\mu$, and typically between about $0.1\mu$ and about $500\mu$ In the devices of the present invention, the microscale channels or chambers preferably have at least one cross-sectional dimension between about $0.1\mu$ and $200\mu$, more preferably between about $0.1\mu$ and $100\mu$, and often between about $0.1\mu$ and $20\mu$. Accor the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

Typically, the microfluidic devices described herein will comprise a top portion, a bottom portion, and an interior portion, wherein the interior portion substantially defines the channels and chambers of the device.

FIG. 3 illustrates a body structure 301, for a microfluidic device. In preferred aspects, the bottom portion of the device comprises a solid substrate that is substantially planar in structure, and which has at least one substantially flat upper surface 305. A variety of substrate materials are optionally employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, printing, and other techniques. The substrate materials are also generally selected for their compatibility with the full range of conditions to which the microfluidic devices are exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See, U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic systems, e.g., provide enhanced fluid direction, e.g., as described in published PCT application, WO 98/05424, and which is incorporated herein by reference in its entirety for all purposes.

The channels and/or chambers or wells of the microfluidic devices are typically fabricated into the upper surface of the bottom substrate, as microscale grooves or indentations, such as first channel region 340, using the above described microfabrication techniques. In the microfluidic devices prepared in accordance with the methods described herein, the top portion also includes a plurality of apertures, such as holes or ports 310, 315, and 320 disposed therethrough.

The first planar surface of the top substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. The holes or wells in the top portion of the device are oriented such that they are in communication with at least one of the channels and/or chambers formed in the interior portion of the device from the grooves or indentations in the bottom substrate. In the completed device, these holes function as reservoirs or wells for facilitating fluid or material introduction into the channels or chambers of the interior portion of the device, as well as providing ports at which electrodes are optionally placed into contact with fluids within the device, allowing application of electric fields and electrokinetic injection or withdrawal of buffer along the channels of the device to control and direct fluid transport within the device. In another embodiment, the holes or wells contain wicks or other absorbent materials to provide for flow and modulation, e.g., for continuous or discontinuous flow applications.

In many embodiments, the microfluidic devices will include an optical detection window disposed across one or more channels and/or chambers of the device. Optical detection windows are typically transparent such that they are capable of transmitting an optical signal from the channel/ chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials are separately manufactured into the device.

These devices are used in a variety of applications, including, e.g., the performance of high throughput screening assays in drug discovery, immunoassays, diagnostics, genetic analysis, call analysis and the like. As such, the devices described herein, will often include multiple sample introduction ports or reservoirs, for the parallel or serial introduction and analysis of multiple samples. Alternatively, these devices are coupled to a sample introduction port, e.g., a pipetor, which serially introduces multiple samples into the device for analysis. Examples of such sample introduction systems are described in e.g., U.S. patent application Ser. Nos. 08/761,575 and 08/760,446 each of which was filed on Dec. 6, 1996, and is hereby incorporated by reference in its entirety for all purposes.

The wells and/or injection ports described above are used in the present invention for electrokinetic injection or withdrawal or placement of a wick or other absorbent materials. The electrokinetic injection or withdrawal and/or wick is then optionally used to control the flow rates through the channels of the device as described above.

Figure 3A:
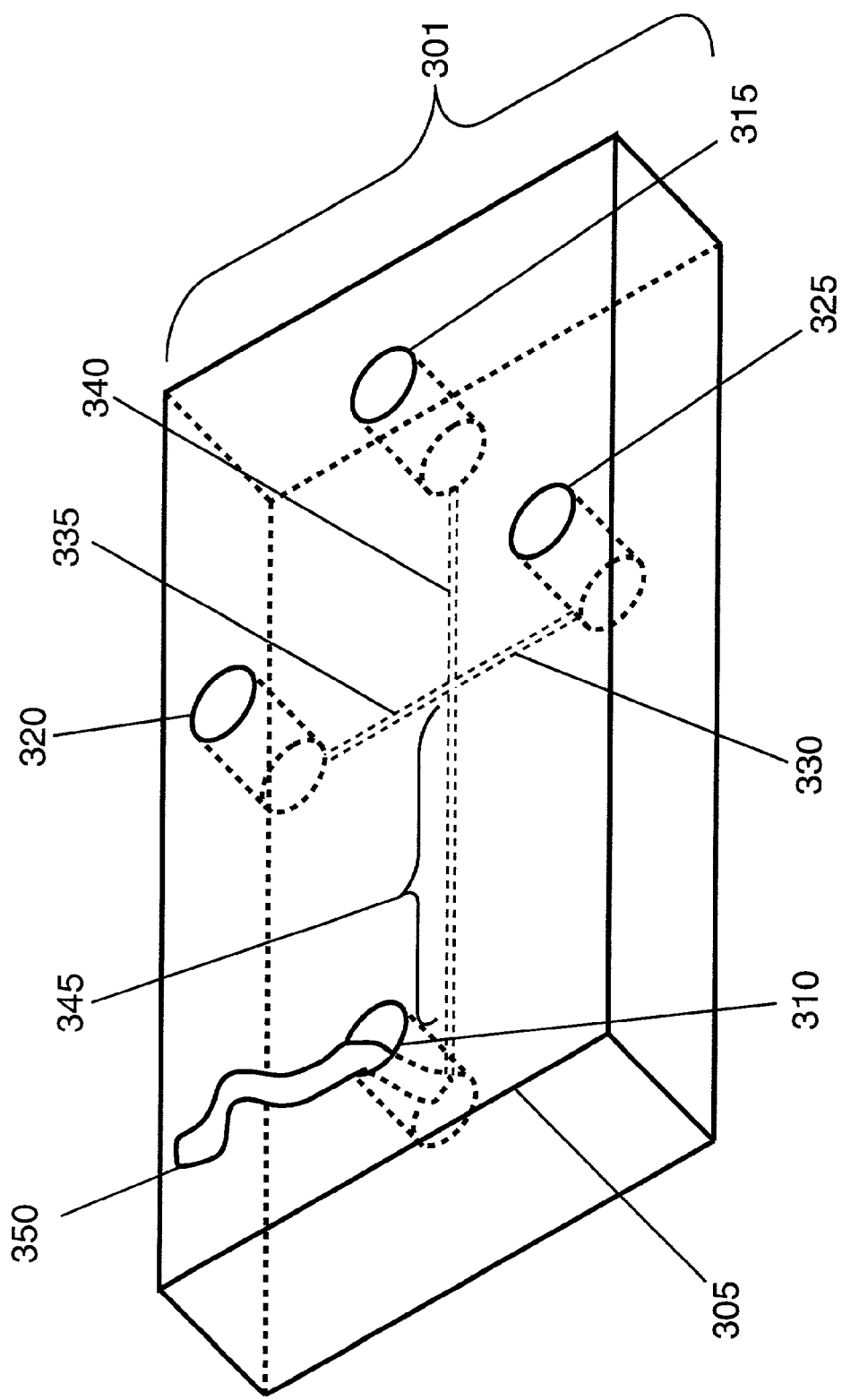
FIG. 3 (panels A, B and C) are schematic drawings of a device comprising an absorbent material such as a wick.

One example is schematically illustrated in FIG. 3A as described. FIGS. 3B and 3C schematically illustrate alternate configurations of the interface between the wick and the microfluidic device. For example, FIG. 3B shows a partial view of the body structure 301 of a microfluidic device that includes a well 310 and a channel 352 fluidly connected to the well 310. A wick 354 is placed into well 310 substantially as described above. In preferred aspects, the wick is a cylindrical bundle of absorbent material, e.g., as described herein, and resembles a cigarette filter in its structure and consistency. The cylindrical shape of the wick allows the wick to be fittedly inserted into a circular well, e.g., well 310, although the shape of the wick can be adjusted to accommodate any well shape. Typically, such cylindrical wicks comprise bundles of fibrous materials which are absorbent in their own right, and/or are absorbent by virtue of their being bundled together as a porous structure, giving rise to capillary-type wicking.

As shown in FIG. 3B, the wick is illustrated as extending well above the upper edge 305 of well 310, to provide a sufficient amount of material to prevent saturation of the wick. Of course, in some instances, a saturated wick may be desirable, e.g., where extremely slow wicking or flow rates are desired. In such cases, wicking from the well 310 will be limited in large part by the rate of evaporation from the wick 354. However, because evaporation rates vary with the relative ambient humidity, it is often desirable for wicking to be non-evaporation limited. Again, this is accomplished in a first aspect by providing a sufficient amount of wicking material. Because fluid volumes in the microfluidic devices of the invention are extremely small, e.g., on the order of microliters deposited in the wells, a wick that merely fills the volume of the well, or is slightly larger, is generally sufficient. Further, larger wicks, with their greater surface areas, typically evaporate greater amounts of fluid, thus reducing the chance that they will reach saturation during the operation to which the device is being put, and thereby preventing evaporation from becoming the rate limiting event.

An alternate wick structure is illustrated in FIG. 3C. As shown, the wick 354 again comprises a cylindrical bundle of absorbent material that is inserted into well 310. However, as shown, the wick 354 includes a cap 358 that substantially seals well 310, to prevent excess evaporation of material in the well, which evaporation can result in faster flow of material from channel 352 into well 310, and in some cases, a faster wicking rate, thereby resulting in a variable flow rate depending upon ambient humidity. In the case of the device shown in FIG. 3C, cap 358 substantially seals well 310 by extending beyond the edge of the wick 354 and overlapping the upper edges 305 of the well 310. In order to prevent back-pressure within the well 310 from slowing or stopping flow, cap 358 includes a vent or hole 360 disposed through it to maintain the well substantially at ambient pressure.

A. Device Integration

Although the devices and systems specifically illustrated herein are generally described in terms of the performance of a few or one particular operation, it will be readily appreciated from this disclosure that the flexibility of these systems permits easy integration of additional operations into these devices. For example, in the present invention, the devices and systems described include methods for detection and monitoring of the materials that are used for the determination of velocity. Since the present invention uses downstream pressure to control the flow rates of materials in the system, downstream devices to control the pressure are included in the system. For example, the devices and systems described will optionally include structures, reagents and systems for performing virtually any number of operations both upstream and downstream from the operations specifically described herein.

Such upstream operations include sample handling and preparation operations, e.g., cell separation, extraction, purification, amplification, cellular activation, labeling reactions, dilution, aliquoting, and the like.

Similarly, downstream operations may include similar operations, including, e.g., separation of sample components, labeling of components, assays and detection operations, electrokinetic injection or withdrawal and wicking. Assay and detection operations include, without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like.

B. Instrumentation

In the present invention, the materials in the channels are monitored and detected so that velocity may be determined. From velocity measurements, decisions are then made regarding flow control mechanisms. Various flow rate control methods, such as a wick or an electrokinetic or pressure based downstream an injection, are then used to control and/or change the measured velocity. Sample incubation times (e.g., for cell samples) are also measured and altered with the above methods. Additional available instrumentation may be used to obtain and analyze these measurements.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretation in a readily accessible reporting format.

C. Controller

A variety of controlling instrumentation is optionally utilized in conjunction with the microfluidic devices described above, for controlling the transport and direction of fluids and/or materials within the devices of the present invention. For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g. U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

As noted above, the systems described herein can utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices. Examples of particularly preferred electrical controllers include those described in, e.g., published PCT application WO 98/05424, the disclosure of which is hereby incorporated herein by reference in its entirety for all purposes. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating undesired temperature effects within the channels.

Typically, the controller systems are appropriately configured to receive a microfluidic device as described herein. In particular, the controller and/or detector (as described in greater detail, below), includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

D. Detector

In the microfluidic systems described herein, a variety of detection methods and systems are employed, depending upon the specific operation that is being performed by the system. Often, a microfluidic system will employ multiple different detection systems for monitoring the output of the system. Detection systems of the present invention are used to detect and monitor the materials in the detection window. Once detected, the flow rate and velocity of particles in the channels is optionally measured and controlled as described above.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source any number of light sources that provides the appropriate wavelength, including lasers, laser diodes and LEDs. Other light sources required for other detection systems. For example, broad band light sources are typically used in light scattering/transmissivity detection schemes, and the like. Typically, light selection parameters are well known to those of skill in the art.

The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

E. Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels, so that flow rate and velocity may be determined. Additionally the software is optionally used to control electrokinetic injection or withdrawal of material. The electrokinetic or withdrawal is used to modulate the flow rate as described above.

F. Kits

Generally, the microfluidic devices described herein are packaged to include many if not all of the necessary reagents for performing the device's preferred function. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for filling the microfluidic channels, e.g., appropriately configured syringes/pumps, or the like. In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Such kits also optionally include an absorbent material that is optionally used as a wick to sustain flow rates as described above. Additionally the kits may come with the wick or absorbent material predisposed in the devices to modulate and/or sustain flow rates. Accordingly, one feature of the invention is the manufacture of microfluidic devices comprising absorbent materials, such as any of these described herein.

The discussion above is generally applicable to the aspects and embodiments of the invention described above.

Moreover, modifications can be made to the method and apparatus described herein without departing from the spirit and scope of the invention as claimed, and the invention can be put to a number of different uses including the following.

The use of a microfluidic system containing at least a first substrate and having a first channel and a second channel intersecting the first channel, at least one of the channels having at least one cross-sectional dimension in a range from 0.1 to 500 $\mu$m, in order to test the effect of each of a plurality of test compounds on a biochemical system. The system including a wick or other absorbent material.

The use of a microfluidic system as described herein, wherein a biochemical system flows through one of said channels substantially continuously, providing for, e.g., sequential testing of said plurality of test compounds.

The use of an absorbent material in a microfluidic device as described herein to modulate or achieve flow in the channels.

The use of an electrokinetic injection in a microfluidic device as described herein to modulate or achieve flow in the channels.

The use of a combination of wicks, electrokinetic injection and pressure based flow elements in a microfluidic device as described herein to modulate or achieve continuous flow in the channels.

An assay utilizing a use of any one of the microfluidic systems or substrates described herein.

Microfluidic devices and bioassays which can be adapted to the present invention include various PCT applications and issued U.S. Patents, such as, U.S. Pat. Nos. 5,699,157 (J. Wallace Parce) issued Dec. 16, 1997, 5,779,868 (J. Wallace Parce et al.) issued Jul. 14, 1998, 5,800,690 (Calvin Y. H. Chow et al.) issued Sep. 1, 1998, and 5,842,787 (Anne R. Kopf-Sill et al.) issued Dec. 1, 1998; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, which are all incorporated herein by reference.

EXAMPLES

The following examples are provided by way of illustration only and not by way of limitation. Those of skill in the art will readily recognize a variety of noncritical parameters that could be changed or modified to yield essentially similar or desirably different results.

Example 1

Control of Flow Rate Using Wicking

Live cells labeled with a fluorescent DNA dye were loaded into a device as in FIG. 3. Cells were detected as they flowed past fluorescent reader in reading area 345. Each peak represents a cell or multiple cells depending how many were in the read area at once.

An empty well was designated as waste well 310, and a piece of Kimwipe™ (3 mm wide and 1.5 cm long) was placed in the waste well, as a wick, so that one end was touching the bottom of the well, and the rest of the piece climbed up and lay flat outside the well on upper surface 305 of the device. A 2.5 microliter pipettor with 2 microliters of liquid in the tip was used to press the wick against the wall of the well. The 2 microliters of liquid was expelled to help start the wicking action. The wick was then lifted from the surface of the microfluidic device to form a bubble as shown in FIG. 3, to facilitate evaporation from the wick to maintain the wicking action.

In other embodiments, evaporation can be limited or eliminated, e.g., by applying a cap to the absorbent material (see e.g., FIG. 3C). A graduated wick, e.g., which has gradually increasing width dimensions can also be used to regulate flow rates.

Figure 7:
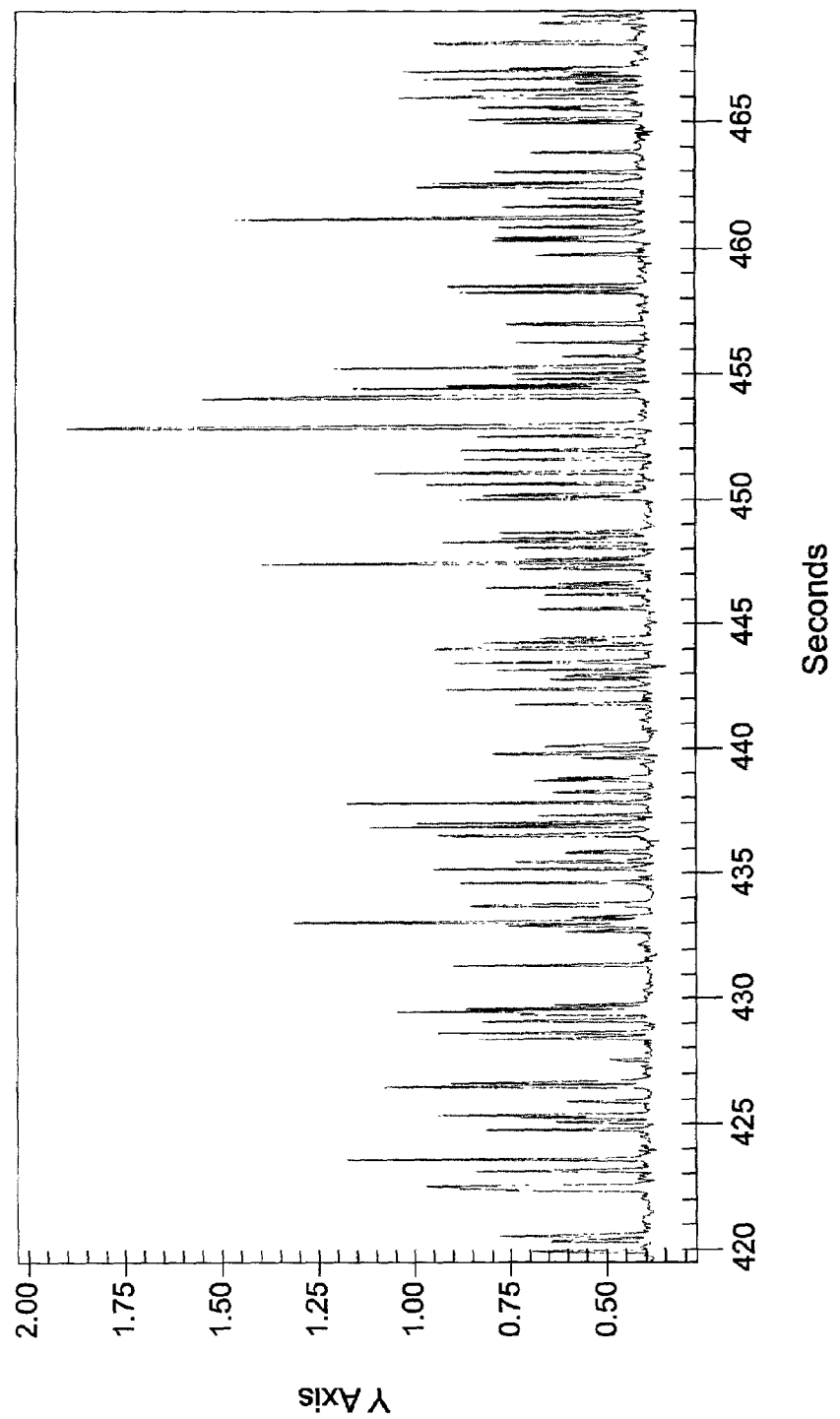
FIG. 7 is a graph of live cells detected using fluorescent DNA dye as they flow through a microfluidic device. The cells are detected as they flow past a fluorescent reader. Each peak represents a cell or multiple cells depending on how many are in the reading area at once. An absorbent material such as a wick was placed into the device at 400 seconds.
Figure 8:
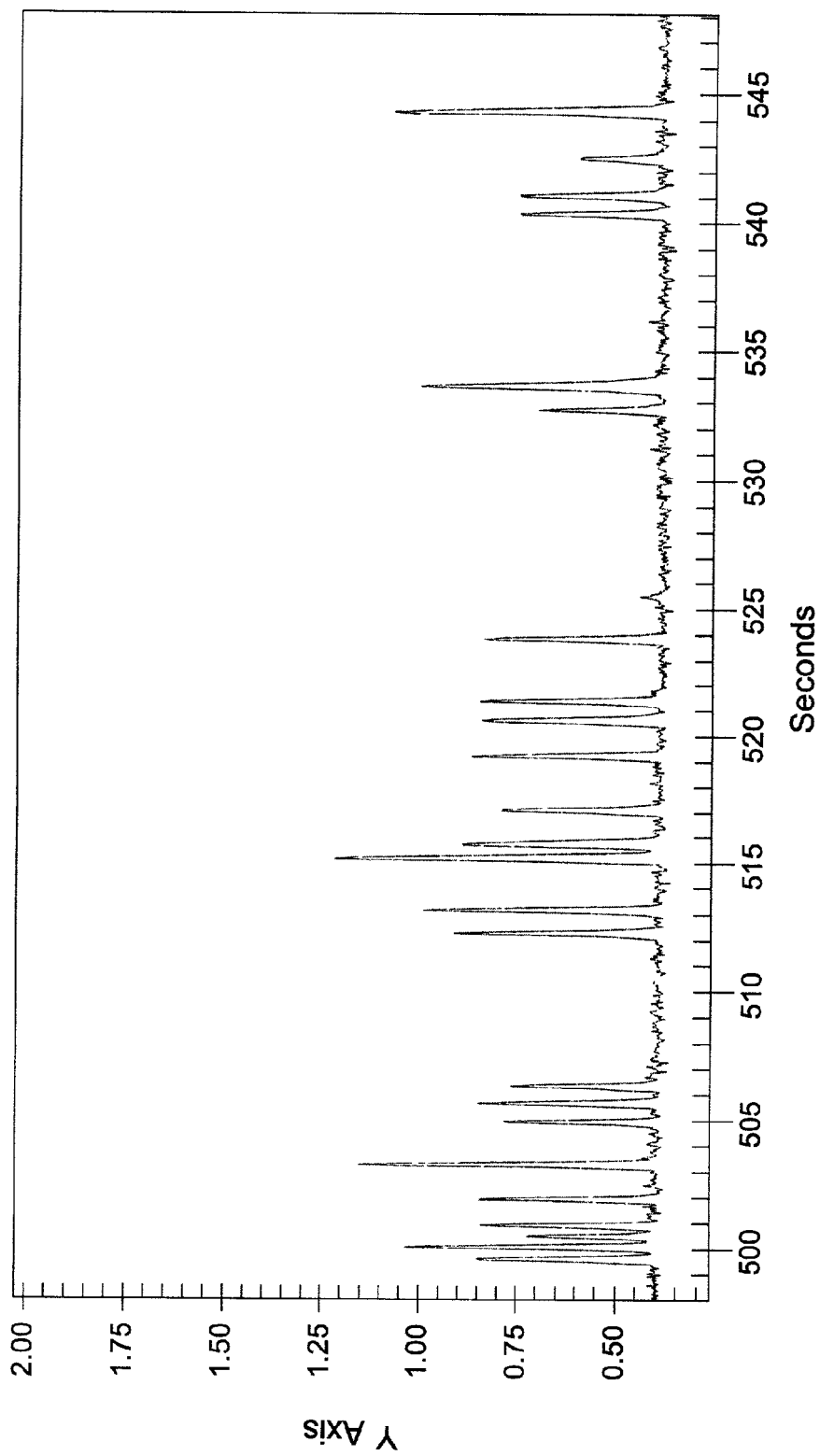
FIG. 8 is a graph of the cells flowing through a microfluidic device after the wick was removed at 500 seconds.
Figure 9:
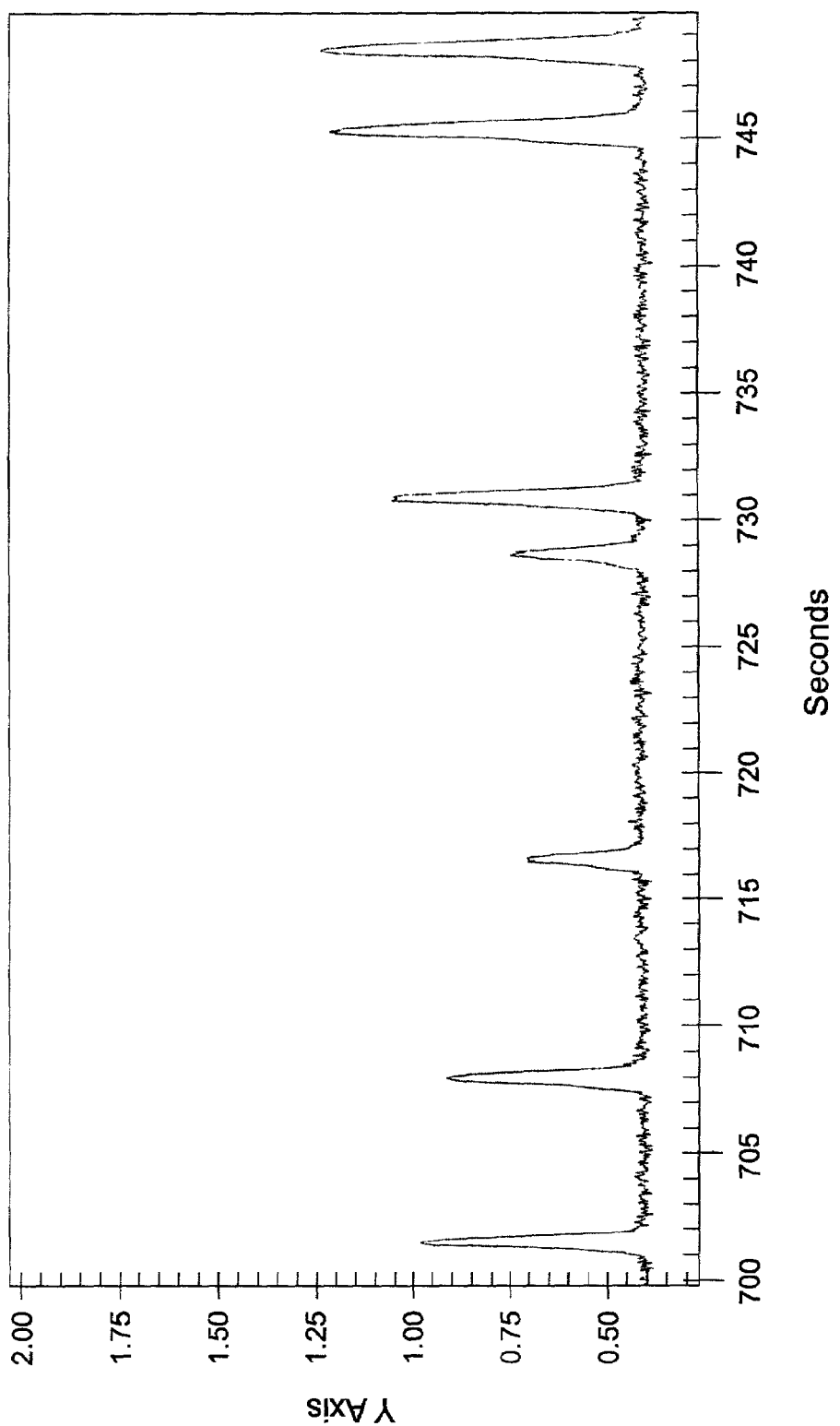
FIG. 9 is a graph of the cells as they flow through a device which does not have a wick in fluidic contact with fluid in the device.
Figure 10:
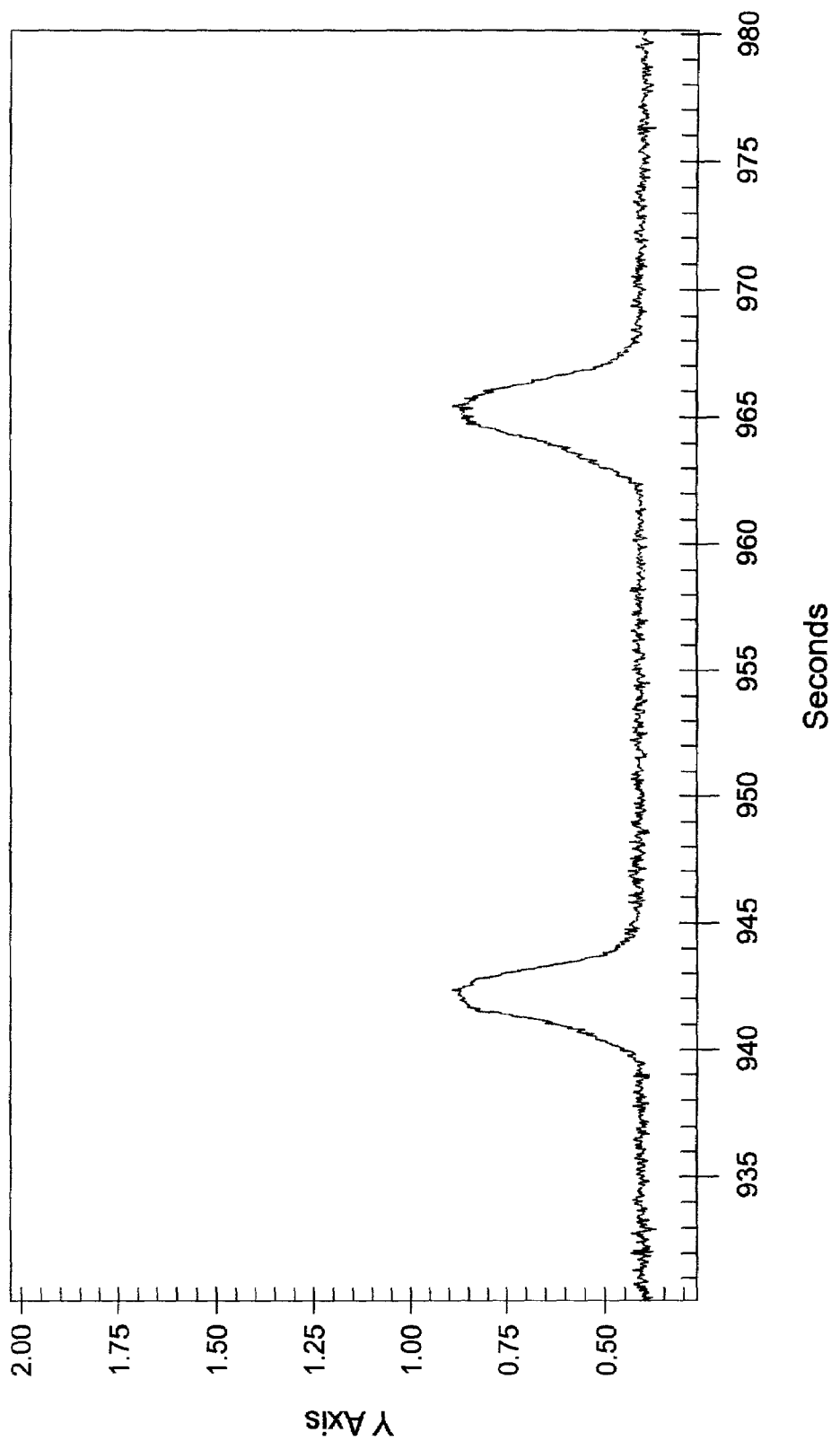
FIG. 10 shows the cells as they stop flowing through a chamber, i.e., with no wick in place, e.g., at about 1000 seconds, or about 500 seconds after the wick was removed.
Figure 11:
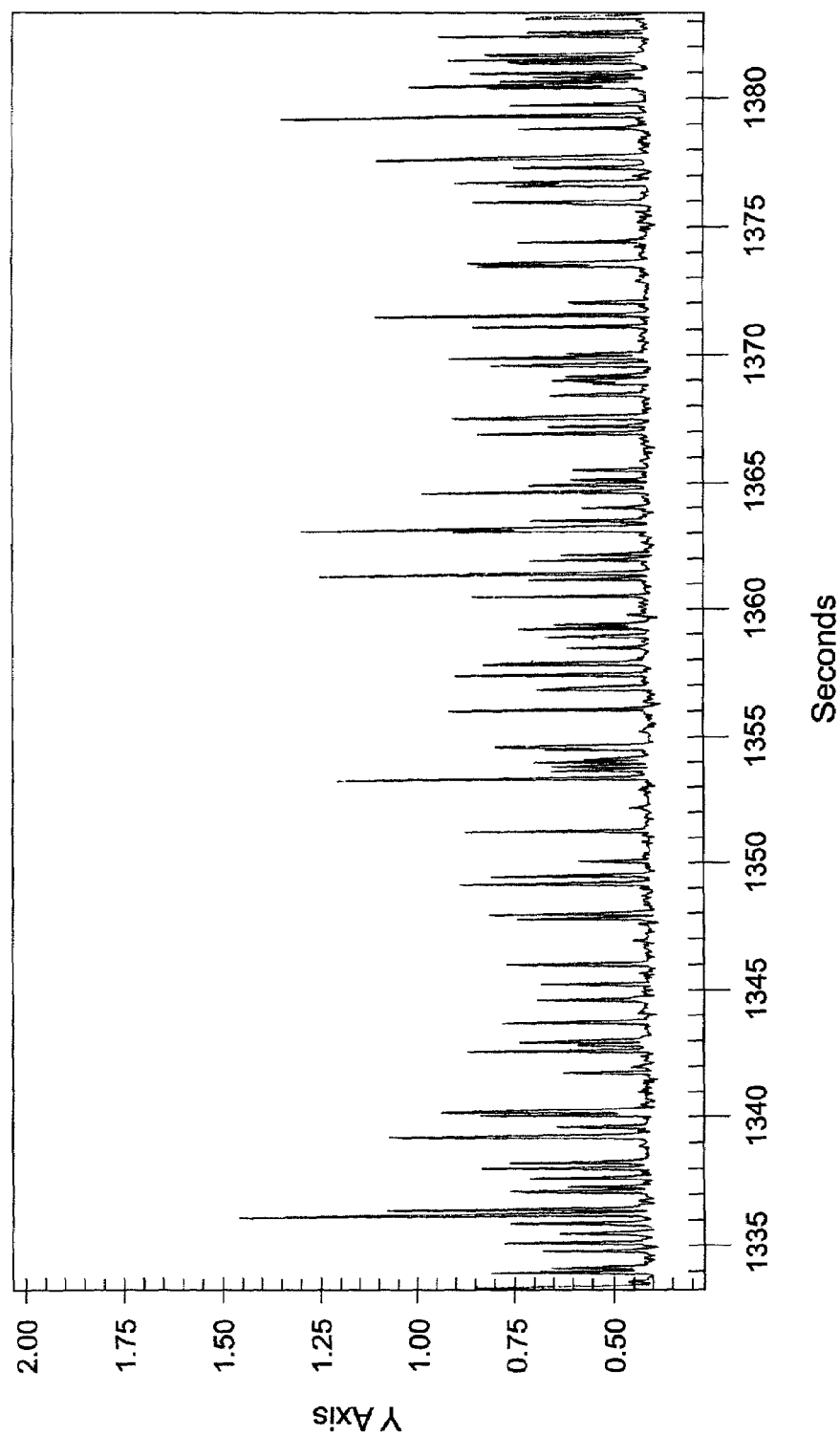
FIG. 11 is a graph showing cells flowing through a device after a wick was replaced at 1300 seconds.
Figure 12:
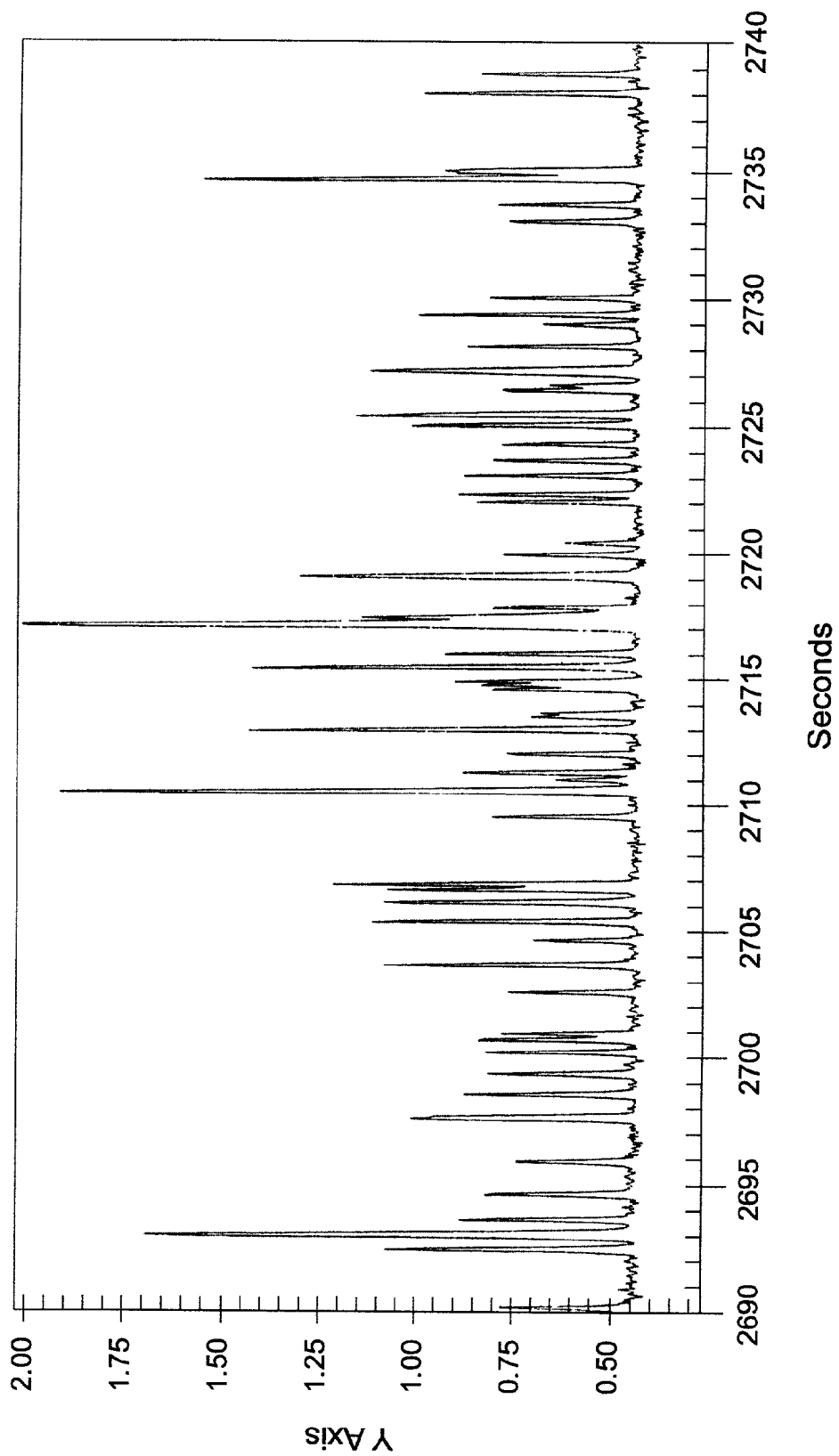
FIG. 12 is a graph showing that the cells continued to flow through the device with a wick in place until at least 2700 seconds, at which time the cells still maintained a high flow rate, evidenced by the narrow peak widths.

Reading was started after the wick was placed in well 310, at about 400 seconds. The detected signals are shown in FIG. 7. The narrow peaks indicate a high flow rate because they flowed through the read area quickly, giving the peak a short duration. FIGS. 8–10-show the effects after the wick was removed at 500 seconds. The flow rate slowed down as shown in FIG. 8, indicated by fewer cells crossing the read area and being detected. In addition, those that were detected were increased in peak width indicating a slower flow rate. At about 1000 seconds, the flow rate eventually stopped without the wick. FIGS. 11 and 12, show the signals detected after the wick was replaced in the well at about 1300 seconds. With the wick functioning to draw the sample through the channels, the flow rate resumed and continued at a good rate. At 2700 seconds, the flow rate was still good as indicated by the narrow peak widths in FIG. 12.

Without a wick to provide continuous flow, the flow rate continued for only 500 seconds compared to 1400 seconds (from 1300 to 2700) of sustained flow using a wick. Therefore, the wick provided convenient method to increase flow rates and sustain them in a microfluidic channel.

Example 2

Control of Flow Rates Using Electrokinetic Injection

Dye Experiments

Figure 2:
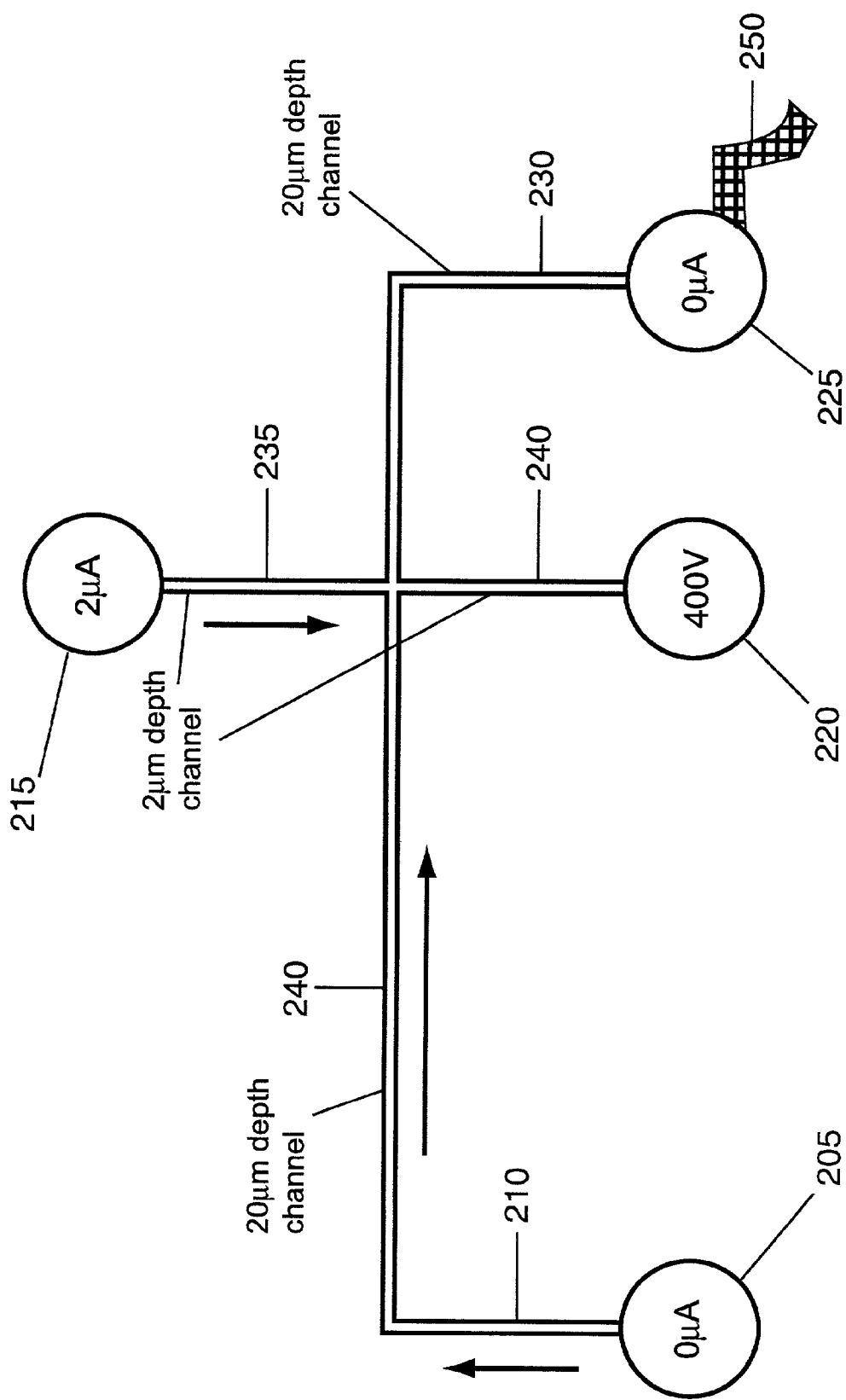
FIG. 2 is a schematic drawing of an alternate device of the invention.

In this experiment, a buffer was injected into side channels of a microfluidic device to demonstrate the ability of side channel electrokinetic injection to rapidly control the flow rate in the main channel of a microfluidic device. A dye was used in the main channel of FIG. 2, with dilution of the dye being an indicator of the effect of side channel buffer injection on the main channel flow rate.

The dye used was Bodipy-Fluorescein (Molecular Probes) dissolved in Hank's Balanced Salt Solution which is the isotonic-high salt buffer added to buffer well 220. The low ionic strength buffer, 30 mM HEPES, pH 7.0 in deionized water, was added to buffer well 215. The wick was a 3 mm strip of Kimwipe, placed in well 225. 10 $\mu$l of each solution was added to buffer well 220 and buffer well 215 respectively. Current was then applied to side channels 235 and 240, and no current to main channel 210 as pictured in FIG. 2. The reading or detecting area was 0.5 mm after the buffer injection intersection in main channel region 245.

Figure 4:
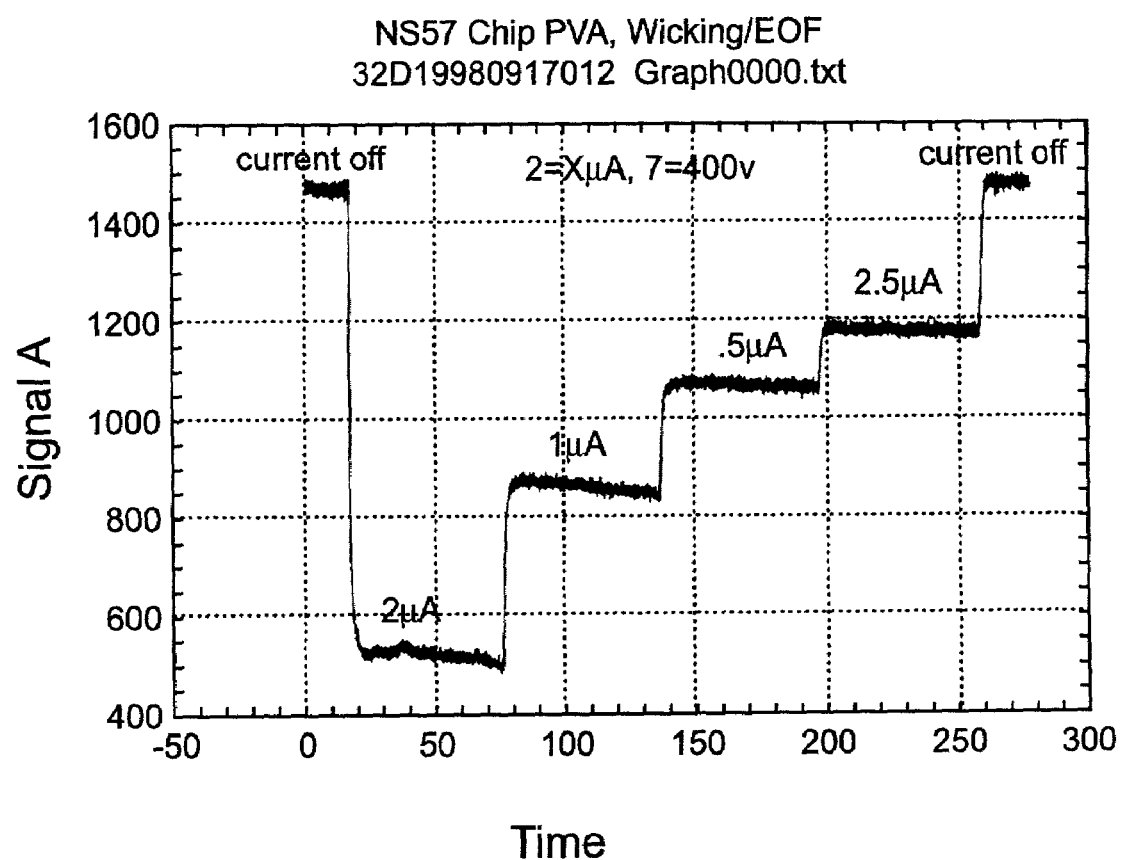
FIG. 4 is a graph showing that as the current is increased for a side-chamber electrokinetic injection into the main chamber, dye in the main chamber is diluted, thereby demonstrating that an effect of the side channel injection is to change the main channel flow rate.
Figure 5:
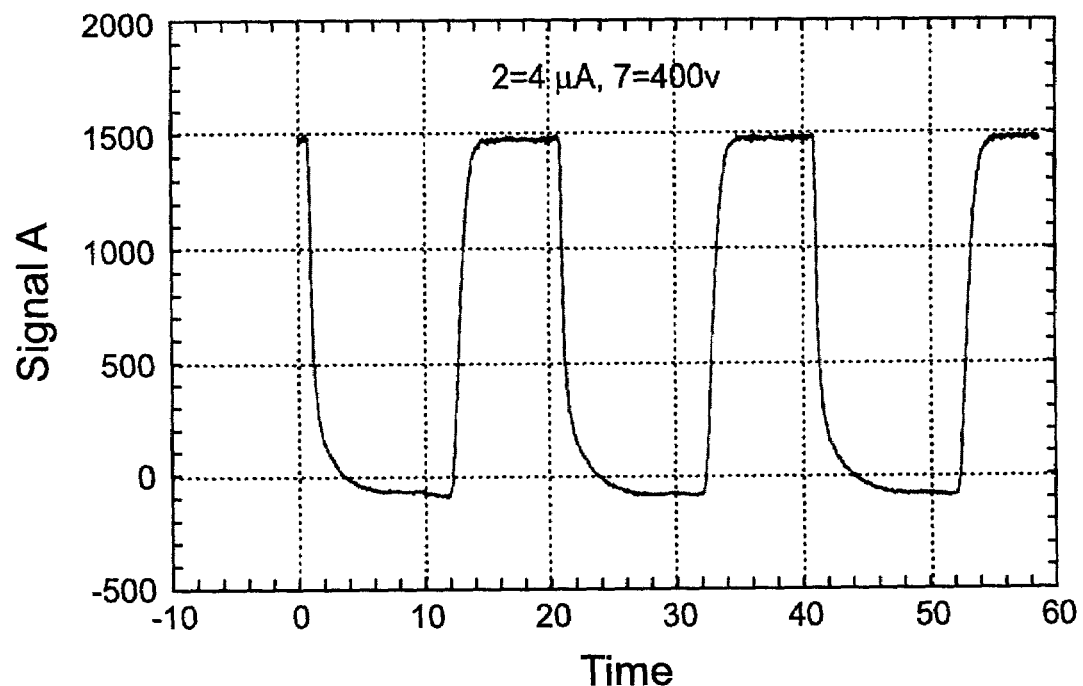
FIG. 5 is a graph showing that toggling an electrokinetic injection current on and off rapidly changes the dilution of a dye in the main chamber, indicating rapid control of flow from a side channel. Time is shown in seconds on the graph and the signal is recorded in relative fluorescence units.

FIG. 4 shows the effect of the buffer from a side channel being injected into the main channel. As the buffer was injected, it diluted the dye in the main channel. This demonstrated the effectiveness of the buffer pumping from the side channel in the present configuration. FIG. 5 shows that toggling the current to the side channels on and off rapidly changes the dilution of the dye in the main channel indicating rapid control of the flow rate from the side channel.

Cell Experiments

After the dye experiment proved the ability of the side channel injection to modulate the flow rate in the main channel, a cell experiment was performed to demonstrate the effect of side channel electrokinetic injection on the velocity of cells in a microfluidic device. In this experiment, the detection area was placed upstream of the buffer injection site, so that no dilution of the cell suspension would occur before detection.

The cells used were THP-1 cells cultured as recommended by the ATCC in RPMI 1640 containing 10% fetal bovine serum, 1 mM pyruvate, 2 mM L-glutamate, 50 $\mu$M β-mercaptoethanol, 10 mM HEPES. The cells were loaded with Calcein-AM dye at 1 $\mu$M for 15 minutes at room temperature in HBSS containing 1 mg/ml BSA, pelleted at 300×g for 5 minutes, and resuspended in Cell Buffer (HBSS containing 1 mg/ml BSA, 20 mM HEPES, 10% w/v Optiprep, specific density adjustment agent). 10 $\mu$l of cell suspension or buffers were added to injection well 205. Low ionic strength buffer was injected as in the dye experiments; however the reading area was 2 mm upstream of the buffer injection, in main channel region 240.

Figure 6:
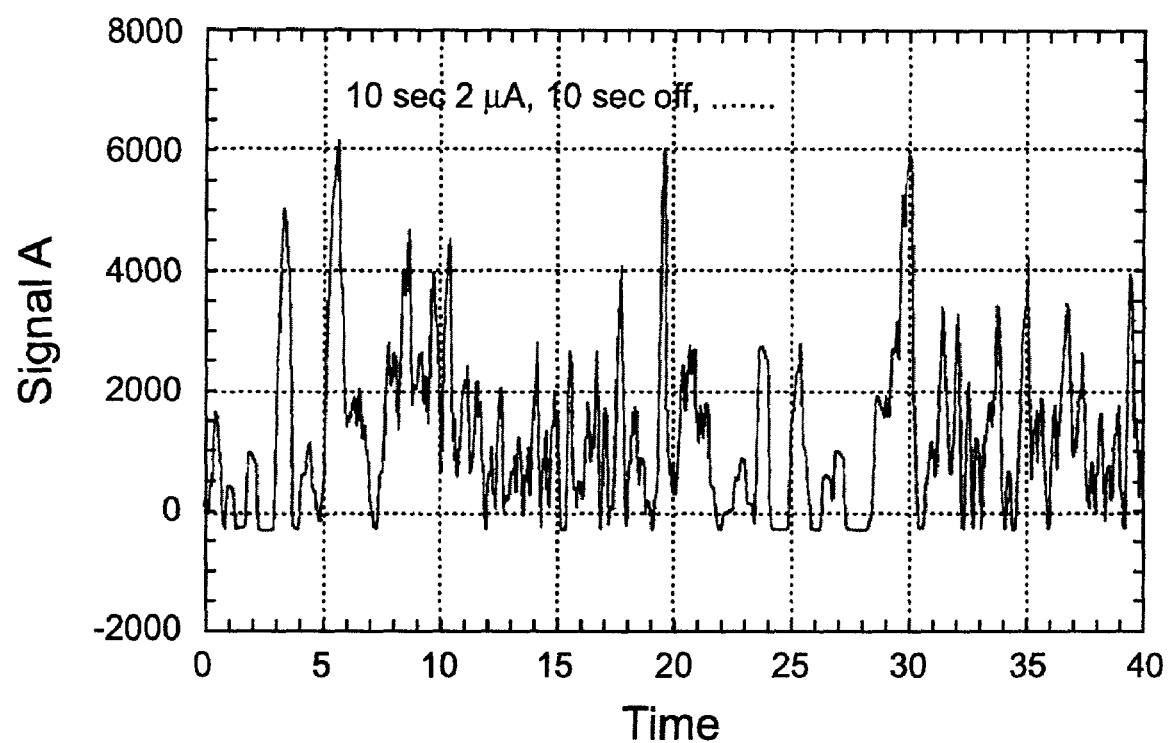
FIG. 6 is a graph showing the effect of buffer injections from the side channel on the flow rate of cells in the main channel.

FIG. 6 shows the effect of buffer injections from the side channel on the flow rate of cells in the main channel. The injection current was toggled from 2 $\mu$A for 10 seconds to 0 for 10 seconds. The width of the peaks as cells pass in front of the fluorescence detector varied with the velocity of the cells. The higher the velocity the narrower the peak. The higher the buffer injection current the slower the cell movement. When the current was turned off, the cell velocity returned to the higher rate.

One of the advantages of this configuration is that the cell velocities are controlled electronically without moving parts, and the electro-osmotically pumped buffer composition can be optimized for pumping efficiency without regard to deleterious effects on the cells since it contacts the cells after the assay measurements are made.

Example 3

Calcium Flux Assay

Using a continuous flow format in planar chips using a wick to generate constant pressure driven flow, cells were mixed with an agonist and down-stream fluorescence detectors were used to monitor indicator cells using Fluo-3 (Molecular Probes Inc.) calcium sensitive fluorescent dye as a probe for receptor activation of calcium fluxes. THP-1 cells were loaded with Fluo-3 by incubation with a 4 $\mu$M concentration of the Fluo-3 AM (acetoxymethyl ester) in Hank's Balanced Salt Solution(HBSS) containing 20 mM HEPES, pH 7.0, and 1 mg/ml bovine serum albumin. After a 40 minute incubation at 37° C., Syto-6, a fluorescent DNA stain, was added to 2.5 $\mu$M, and the cells were incubated for an additional 10 minutes at room temperature. The cells were then washed free of excess dye by pelleting at 300×g for 5 minutes and resuspending and repelleting. The cells were resuspended in Cell Buffer (HBSS containing 20 mM HEPES, pH 7.0, 1 mg/ml BSA and 10% Optiprep). The THP-1 cells were tested for UTP-activated calcium fluxes mediated through the purinergic, P2Y receptor by adding different concentrations of UTP from 0–3 $\mu$M to the cells in the microfluidic device and detecting the calcium response using a blue LED to excite the intracellular Fluo-3 and the Syto-62.

Figure 13:
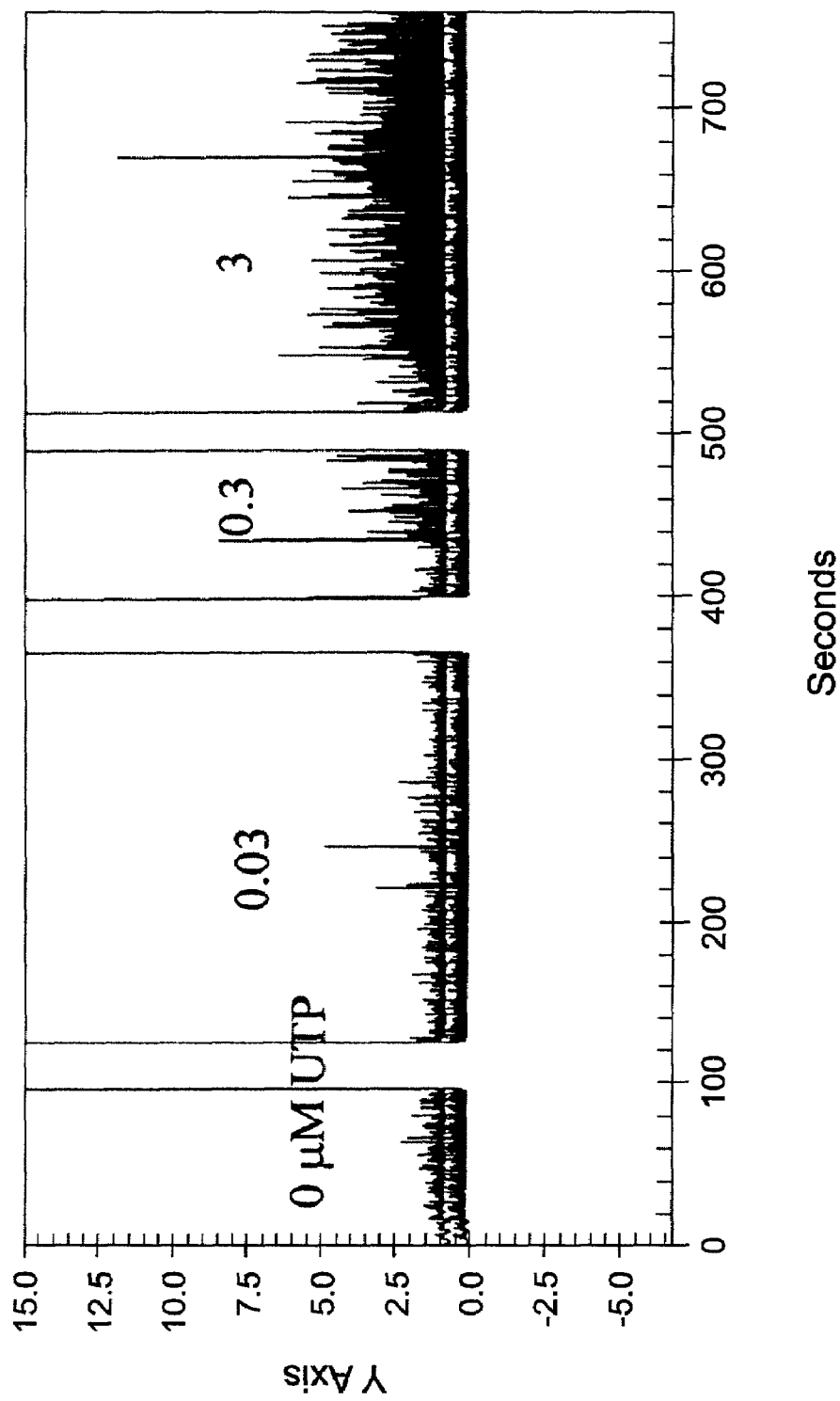
FIG. 13 shows graphs from a calcium flux assay performed using the devices of the invention.

The results of these tests are displayed in FIG. 13 showing the spikes of fluorescence as the cells pass the detector. The lower trace shows that the fluorescence of the DNA staining dye is not affected by the UTP treatment, and the upper trace shows that the fluorescence of the calcium sensitive dye increases with UTP treatment in a dose dependent manner, indicating an increase in intracellular free calcium. By taking the ratio of the two fluorescent dyes, it is possible to normalize the calcium flux response in the THP-1 cells since the DNA staining intensity is a constant in diploid, resting cells, and thereby quantitate the increase in calcium concentration.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed:

1. A microfluidic device comprising:
   (i) a body structure having at least two intersecting microchannels fabricated therein;
   (ii) a reservoir fluidly coupled to the at least two intersecting microchannels and having an aperture allowing external access to the body structure; and,
   (iii) a wick positioned within the reservoir in fluidic communication with the at least two intersecting microchannels, which wick is configured to modulate fluid flow in the at least two intersecting microchannels during operation of the device.

2. The device of claim 1, wherein the wick is positioned downstream from a junction between the at least two intersecting microchannels.

3. The device of claim 1, wherein the wick is positioned at a junction between one of the at least two intersecting microchannels and the reservoir, wherein by the wick is configured to absorb fluid from the reservoir and at least one of the two intersecting microchannels.

4. The device of claim 1, wherein the wick comprises an absorbent material selected from: a solid material, a porous material, a gel, a polymer, a high salt fluid, a thermoplastic polymer, a porous plastic material, and a polyolefin resin.

5. The device of claim 4, wherein the absorbent material is selected from: paper, dried polyacrylamide, dry sephadex, a dextran particle, a polyethylene particle, a polypropylene particle, a high molecular weight polyethylene particle, a polyvinylidene fluoride particle, an ethylene-vinyl acetate particle, a polytetrafluoroethylene particle, a styrene-acrylonitril particle, a polysulfone particle, a polycarbonate particle, a polythalate particle, and combinations thereof.

6. The device of claim 4, wherein the absorbent material further comprises a surfactant.

7. The device of claim 1, wherein the wick is pre-wetted prior to placement in the reservoir.

8. The device of claim 1, wherein the wick is not pre-wetted prior to placement in the reservoir.

9. The device of claim 1, wherein the reservoir is a waste well.

10. The device of claim 1, wherein the reservoir has an upper edge and wherein the wick projects beyond the upper edge.

11. The device of claim 1, wherein the wick is positioned entirely within the reservoir.

12. The device of claim 1, wherein the body structure further comprises a network of capillaries.

13. The device of claim 1, further comprising a detector operably coupled to the device for monitoring a flow rate of one or more materials within the two intersecting microchannels.

* * * * *